United States Patent [19]

(12) United States Patent
Tung

(10) Patent No.: US 7,863,274 B2
(45) Date of Patent: Jan. 4, 2011

(54) DEUTERIUM ENRICHED ANALOGUES OF TADALAFIL AS PDE5 INHIBITORS

(75) Inventor: Roger Tung, Lexington, MA (US)

(73) Assignee: Concert Pharmaceuticals Inc., Lexington, MA (US)

( * ) Notice: Subject to any disclaimer, the term of this patent is extended or adjusted under 35 U.S.C. 154(b) by 426 days.

(21) Appl. No.: 11/704,555

(22) Filed: Feb. 8, 2007

(65) Prior Publication Data

US 2007/0191381 A1 Aug. 16, 2007

Related U.S. Application Data

(63) Continuation-in-part of application No. 11/498,305, filed on Jul. 31, 2006, now abandoned.

(60) Provisional application No. 60/703,570, filed on Jul. 29, 2005, provisional application No. 60/703,612, filed on Jul. 29, 2005.

(51) Int. Cl.
*A61K 31/4985* (2006.01)
(52) U.S. Cl. .................. 514/250; 544/343
(58) Field of Classification Search .................. 544/343
See application file for complete search history.

(56) References Cited

U.S. PATENT DOCUMENTS

| 5,859,006 | A | 1/1999 | Daugan | |
|---|---|---|---|---|
| 6,221,335 | B1 * | 4/2001 | Foster | 424/1.81 |
| 6,440,710 | B1 * | 8/2002 | Keinan et al. | 435/148 |
| 6,603,008 | B1 * | 8/2003 | Ando et al. | 546/269.7 |
| 7,517,990 | B2 * | 4/2009 | Ito et al. | 546/184 |
| 2004/0186046 | A1 | 9/2004 | Burgess et al. | |
| 2005/0154024 | A1 | 7/2005 | Bryans | |
| 2007/0037815 | A1 | 2/2007 | Tung | |
| 2007/0082929 | A1 * | 4/2007 | Gant et al. | 514/338 |
| 2007/0197695 | A1 * | 8/2007 | Potyen et al. | 524/110 |
| 2008/0103122 | A1 | 5/2008 | Veltri | |

FOREIGN PATENT DOCUMENTS

WO WO-95/26325 10/1995
WO WO 2007/146124 * 12/2007

OTHER PUBLICATIONS

West, Anthony R., Solid State Chemistry and its Applications, Wiley, New York, 1988, pp. 358 and 365.*
Wolff, Manfred E. "Burger's Medicinal Chemistry, 5ed, Part I", John Wiley & Sons, 1995, pp. 975-977.*
Banker (Modern Pharmaceutics) Banker, G.S. et al, "Modern Pharmaceutics, 3ed.", Marcel Dekker, New York, 1996, pp. 451 and 596.*
Dyck, Journal of Neurochemistry vol. 46 Issue 2, pp. 399-404 (1986).*
Tonn, Biological Mass Spectrometry vol. 22 Issue 11, pp. 633-642 (1993).*
Haskins, Biomedical Spectrometry vol. 9 Issue 7, pp. 269-277 (1982.*
Wolen, Journal of Clinical Pharmacology 1986; 26: 419-424.*
Browne, Journal of Clinical Pharmacology1998; 38: 213-220.*
Baillie, Pharmacology Rev.1981; 33: 81-132.*
Gouyette, Biomedical and Environmental Mass Spectrometry, vol. 15, 243-247 (1988).*
Cherrah, Biomedical and Environmental Mass Spectrometry vol. 14 Issue 11, pp. 653-657 (1987).*
Pieniaszek, J Clin Pharmacol.1999; 39: 817-825.*
Honma et al., Drug Metab Dispos 15 (4): 551 (1987).*
Fisher, Michael B. et al: "The Complexities Inherent in Attempts to Decrease Drug Clearance by Blocking Sites of CYP-Mediated Metabolism," Drug Discovery & Development 2006 vol. 9 No. 1.
Foster, Allan B.: "Deuterium Isotope Effects in Studies of Drug Metabolism," TIPS—Dec. 1984 524-527.
Kushner, D.J. et al: "Pharmacological Uses and Perspectives of Heavy Water and Deuterated Compounds," Can. J. Physiol. Pharmacol 77: 79-88 (1999).
Prescribing information for CIALIS® (tadalafil), accessed at http://www.cialis.com (revised in 2007).
Silvestro et al., "Human Pharmacokinetics of Glycosaminoglycans Using Deuterium-Labeled and Unlabeled Substances: Evidence for Oral Absorption", Seminars in Thrombosis and Hemostasis, vol. 20, No. 3, pp. 281-292, 1994.

(Continued)

*Primary Examiner*—James O Wilson
*Assistant Examiner*—Brian McDowell
(74) *Attorney, Agent, or Firm*—Edwards Angell Palmer & Dodge LLP; Jeffrey D. Hsi; Mark D. Russett

(57) ABSTRACT

The present invention relates to derivatives of tadalafil represented by the formula:

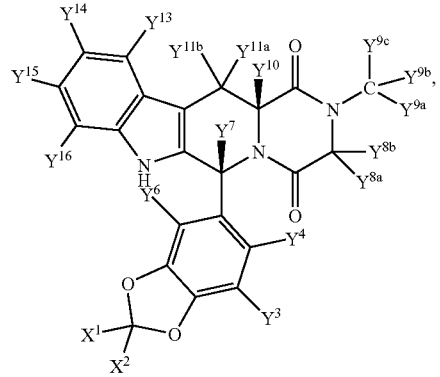

or a salt thereof, wherein:
$X^1$ and $X^2$ are simultaneously fluoro; or $X^1$ is deuterium and $X^2$ is selected from hydrogen or deuterium;
each Y is independently selected from deuterium or hydrogen;
the hydrogen attached to the indole nitrogen is optionally replaced by deuterium; and
each carbon is independently optionally replaced by $^{13}C$. These compounds are selective PDE5 inhibitors and possess advantageous biopharmaceutical and pharmacokinetic properties. The invention further provides compositions comprising these compounds and methods of treating diseases and conditions that are responsive to PDE5 inhibition, alone and in combination with additional agents.

4 Claims, No Drawings

OTHER PUBLICATIONS

Jarman et al., "The deuterium isotope effect for the α-hydroxylation of tamoxifen by rat liver microsomes accounts for the reduced genotoxicity of [$D_5$-ethyl]tamoxifen", Carcinogenesis, vol. 16, No. 4, pp. 683-688, 1995.

Baker et al., "Inhibitory Effects of Deuterium Substitution on the Metabolism of Sevoflurane by the Rat", Drug Metabolism and Disposition, vol. 21, No. 6, pp. 1170-1171, 1993.

Spielmann et al., "Embroyotoxicity of Stable Isotopes and Use of Stable Isotopes in Studies of Teratogenetic Mechanisms", J Clin Pharmacol, 1986:26: 474-480.

van Beerendonk et al., "Genotoxicity of the flame retardant tris(2,3-dibromopropyl)phosphate in the rat and *Drosophila*: effects of deuterium substitution", Carcinogenesis, vol. 15, No. 6, pp. 1197-1202, 1994.

Van Langenhove, "Isotope Effects: Definitions and Consequences for Pharmacologic Studies", J Clin Pharmacol 26:383-389, 1986.

Wenzel, "Increased Brain Affinity of [131]Iodo-labelled N-(alkyl) Amphetamines following Deuteration", Journal of Labelled Compounds and Radiopharmaceuticals, vol. XXVII, No. 10 (in German with English translation).

Nelson et al., "Deuterium Isotope Effects on the Metabolism and Toxicity of Phenacetin in Hamsters", Drug Metabolism and Disposition, vol. 6, No. 4, pp. 363-367, 1978.

Foster, "Deuterium isotope effects in studies of drug metabolism", TIPS, Dec. 1984, pp. 524-527.

Foster, "Deuterium Isotope Effects in the Metabolism of Drugs and Xenobiotics: Implications for Drug Design", Advances in Drug Research, vol. 14, pp. 1-40, 1985.

Fukuto et al., "Determination of the Mechanism of Demethylenation of (Methylenedioxy) phenyl Compounds by Cytochrome P450 Using Deuterium Isotope Effects", J. Med. Chem, 1991, 34, 2871-2876.

Loftus et al., "Metabolism and Pharmacokinetics of Deuterium-Labelled Di-2-(Ethylhexyl) Adipate (DEHA) in Humans", Fd Chem. Toxic., vol. 31, No. 9, pp. 609-614, 1993.

Mabic et al., "Regioselective Synthesis of Deuterated Analogs of the Neurotoxin MPTP", Journal of Labelled Compounds and Radiopharmaceuticals, vol. XXXVIII, No. 3, pp. 255-262, 1996.

Nelson, "The Use of Stable and Radioactive Isoopes in Monitoring Reactive Metabolite Formation", in *Synthesis and Applications of Isotopically Labeled Compounds*. Proceedings of an International Symposium, Kansas City, MO, U.S.A., Jun. 6-11, 1982, pp. 89-94.

Scobie et al., "Labelled Compounds of Interest as Antitumour Agents. Part 4. Deuteration and Tritiation of a Nitrolmidazole-Carborane Designed for BNCT", Journal of Labelled Compounds and Radiopharmaceuticals, vol. XXXIV, No. 9, pp. 881-885, 1994.

Tsuzuki et al., "Ultrasound-Assisted Reduction of Cyanides to Deuteriated Aliphatic Amines", Journal of Labelled Compounds and Radiopharmaceuticals, vol. XXXVIII, No. 4, pp. 385-393, 1996.

Vandenheuvel, "The Use of Stable and Radioactive Isotopes in Drug Metabolism Studies", in *Syntheses and Applications of Isotopically Labeled Compounds*. Proceedings of an International Symposium, Kansas City, MO, U.S.A., Jun. 6-11, 1982, pp. 77-82.

Webb et al., "Labelled Compounds of Interest as Antitumour Agents. Part II (1). Synthesis of $^2$H and $^3$H Isotopomers of RSU 1069 and Ro 03-8799 (PIMONIDAZOLE)", Journal of Labelled Compounds and Radiopharmaceuticals, vol. XXVIII, No. 3, 1990, pp. 257-264.

Yang et al., "Synthesis of 3-Deuterated Diazepam and Nordiazepam 4-Oxides and Their Use in the Synthesis of Other 3-Deuterated Derivatives", Journal of Labelled Compounds and Radiopharmaceuticals, vol. XXXVIII, No. 8, 1996, pp. 753-759.

McCarty et al., "The Effects of Deuteration on the Metabolism of Halogenated Anesthetics in the Rat", Anesthesiology, 51:106-110, 1979.

Mazier et al., "Diet Fat Saturation and Feeding State Modulate Rates of Cholesterol Synthesis in Normolipidemic Men", J. Nutr., 127:332-340, 1997.

Mosberg et al, "Synthesis of Deuterium Labelled Penicillamine and Its Use for the Assignment of the $^1$H NMR Spectra of Two Cyclic Enkephalin Analogs", Journal of Labelled Compounds and Radiopharmaceuticals, vol. XXIV, No. 10, pp. 1265-1271, 1987.

Munro et al., "Plasma RRR-α-tocopherol concentrations are lower in smokers than in non-smokers after ingestion of a similar oral load of this antioxidant vitamin", Clinical Science (1997) 92, 87-93.

Avery et al., "Deuterated Antimalarials: Synthesis of Trideutero-Artemisinin, Dihydroartemisinin, and Arteether", Journal of Labelled Compounds and Radiopharmaceuticals, vol. XXXVIII, No. 3, pp. 249-254, 1996.

Castell et al., "A General Procedure for Isotopic (Deuterium) Labelling of Non-Steroidal Antiinflammatory 2-Arylpropionic Acids", Journal of Labelled Compounds and Radiopharmaceuticals, vol. XXXIV, No. 1, pp. 93-100, 1994.

Ferraboschi et al., "A Facile Synthesis of Pentadeuterated Domiodol (2-Iodomethyl-4-Hydroxymethyl-1,3-Dioxolane) From Glycerol-1,1,2,3,3-$d_5$", Journal of Labelled Compounds and Radiopharmaceuticals, vol. XXXIV, No. 3, pp. 303-306, 1994.

Hinz et al., "Stabilities of $^3$H- and $^2$H-labelled Camptothecins", Journal of Labelled Compounds and Radiopharmaceuticals, vol. XXXVIII, No. 8, pp. 733-742, 1996.

International Search Report in corresponding PCT Patent Application No. PCT/US2006/029461.

International Preliminary Report on Patentability in corresponding PCT Patent Application No. PCT/US2006/029461.

Park, B.K. et al.,"Metabolism of fluorine-containing drugs", Annu. Rev. Pharmacol. Toxicol., 41:443-70 (2001).

* cited by examiner

DEUTERIUM ENRICHED ANALOGUES OF TADALAFIL AS PDE5 INHIBITORS

CROSS REFERENCE TO RELATED APPLICATIONS

This application is a continuation-in-part of U.S. patent application Ser. No. 11/498,305, filed Jul. 31, 2006, which claims benefit of U.S. provisional application 60/703,570, filed Jul. 29, 2005, and U.S. provisional application 60/703,612, filed Jul. 29, 2005, the contents of each is incorporated by reference herein.

TECHNICAL FIELD OF THE INVENTION

The present invention relates to derivatives novel isotopologues of tadalafil, (also referred to herein as "Compound 1"), substituted with fluorine and/or deuterium on the methylene carbon atom situated between the oxygens of the benzodioxol ring, optionally further substituted with deuterium atoms in place of normally abundant hydrogen, and $^{13}C$ in place of normally abundant $^{12}C$. The compounds of this invention are selective inhibitors of cyclic guanosine monophosphate-specific phosphodiesterase type 5 (PDE5) and possess unique biopharmaceutical and pharmacokinetic properties compared to tadalafil. The invention further provides compositions comprising a compound of this invention and the use of such compositions in methods of treating diseases and conditions beneficially treated by PDE5 inhibition, particularly those relating to sexual dysfunction. The invention also provides methods for the use of a deuterium- or $^{13}C$-containing compound of this invention to determine concentrations of Compound 1, particularly in biological fluids, and to determine metabolism patterns of Compound 1.

BACKGROUND OF THE INVENTION

Compounds of Formula I have been disclosed as potent and medically useful inhibitors of cyclic guanosine monophosphate-specific phosphodiesterase type 5 (PDE5). Daugan A C-M, U.S. Pat. No. 5,859,006 to ICOS; Daugan A C-M and Gellibert F, U.S. Pat. No. 6,143,746 to ICOS:

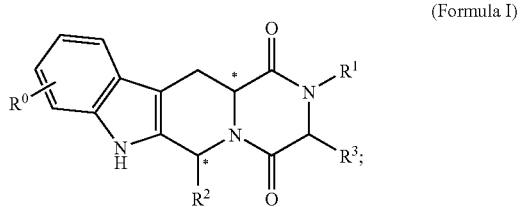

(Formula I)

or salts of solvates thereof, in which: $R^0$ represents hydrogen, halogen or $C_{1-6}$ alkyl; $R^1$ represents hydrogen, $C_{1-6}$ alkyl, $C_{2-6}$ alkenyl, $C_{2-6}$ alkynyl, halo$C_{1-6}$ alkyl, $C_{3-8}$cycloalkyl, $C_{3-8}$cycloalkyl, $C_{1-3}$alkyl, aryl$C_{1-3}$alkyl, wherein aryl is phenyl or phenyl substituted with one to three substituents selected from the group consisting of halogen, $C_{1-6}$ alkyl, $C_{1-6}$ alkoxy, methylenedioxy, and mixtures thereof, or heteroaryl$C_{1-3}$alkyl, wherein heteroaryl is thienyl, furyl, or pyridyl, each optionally substituted with one to three substituents selected from the group consisting of halogen, $C_{1-6}$ alkyl, $C_{1-6}$ alkoxy, and mixtures thereof; $R^2$ represents an optionally substituted mono-cyclic aromatic ring selected from benzene, thiophene, furan and pyridine or an option each of which are incorporated herein in their entirety ally substituted bicyclic ring

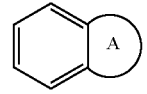

attached to the rest of the molecule via one of the benzene ring carbon atoms and wherein the fused ring A is a 5- or 6-membered ring which may be saturated or partially or fully unsaturated and comprises carbon atoms and optionally one or two heteroatoms selected from oxygen, sulfur, and nitrogen; and $R^3$ represents hydrogen or $C_{1-3}$ alkyl, or $R^1$ or $R^3$ together represents a 3- or 4-membered alkyl or alkenyl chain component of a 5- or 6-membered ring.

Compound 1, chemically described variously as pyrazino[1',2':1,6]pyrido[3,4-b]indole-1,4-dione, 6-(1,3-benzodioxol-5-yl)-2,3,6,7,12,12a-hexahydro-2-methyl-, (6R,12aR)-; as (6R,12aR)-6-(1,3-benzodioxol-5-yl)-2-methyl-1,2,3,4,6,7,12,12a-octahydropyrazino[1',2':1,6]pyrido[3,4-b]indole-1,4-dione; and as (6R,12aR)-2,3,6,7,12,12a-hexahydro-2-methyl-6-(3,4-methylenedioxyphenyl)pyrazino [2',1':6,1]pyrido[3,4-b]indole-1,4-dione;

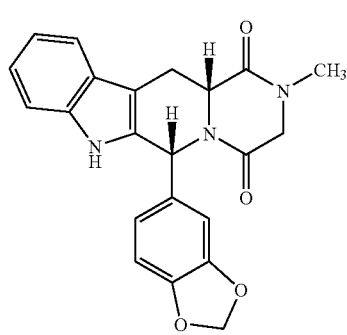

(Compound I)

comprises a particularly important example of this genus.

Compound 1 and pharmaceutical compositions comprising it have utility both alone and, for certain conditions, in combination with additional agents, for the treatment of: erectile dysfunction, stable, unstable and variant angina, hypertension, pulmonary hypertension, chronic obstructive pulmonary disease, acute respiratory distress syndrome, malignant hypertension, pheochromocytoma, congestive heart failure, acute renal failure, chronic renal failure, atherosclerosis, conditions of reduced blood vessel patency, peripheral vascular diseases, vascular disorders, thrombocythemia, inflammatory diseases, myocardial infarction, stroke, bronchitis, chronic asthma, allergic asthma, allergic rhinitis, glaucoma, peptic ulcer, gut motility disorders, postpercutaneous transluminal coronary or carotid angioplasty, post-bypass surgery graft stenosis, osteoporosis, preterm labor, benign prostatic hypertrophy, and irritable bowel syndrome, in humans and in animals; erectile dysfunction in male humans and animals; and female arousal disorder in females. Daugan A C-M and Gellibert F, U.S. Pat. No. 6,143,746 to ICOS; Daugan A C-M, U.S. Pat. No. 6,140,329 to ICOS; Daugan A C-M, U.S. Pat. No. 5,859,006 to ICOS; Anderson N R and Gullapalli R P, U.S. Pat. No. 6,841,167 to Lilly Icos; Allemeier L L et. al., U.S. Pat. No. 6,613,768 to Lilly Icos.

Definitions and descriptions of these conditions are known to the skilled practitioner and are further delineated, for instance, in the above patents and references contained therein; Harrison's Principles of Internal Medicine 16th Edition, Kasper D L et. al. Eds., 2004, McGraw-Hill Professional; and Robbins & Cotran Pathologic Basis of Disease, Kumar V et. al. Eds., 2004, W. B. Saunders. Compound 1 is currently indicated for the treatment of erectile dysfunction. United States Food and Drug Administration (FDA) New Drug Application (NDA) no. 021368; see label approved on Mar. 31, 2005; http://www.fda.gov/cder/foi/label/2005/021368s004,005lbl.pdf.

The combination of Compound 1 with additional agents extends or enhances its utility in the treatment of sexual deficient states in humans, including those with epilepsy, craniopharyngioma, hypogonadism, or who have had a hysterectomyoophorectomy, hysterectomy or oophorectomy; and to the induction of mating in non-human animals. McCall R B and Meglasson M D, U.S. Pat. No. 6,903,127 to Pharmacia & Upjohn; McCall R B and Meglasson M D, U.S. Pat. No. 6,890,945 to Pharmacia & Upjohn; McCall R B and Meglasson M D, U.S. Pat. No. 6,809,112 to Pharmacia & Upjohn. See also Shapira N, US Patent Application 20040009957; Adams M A et. al. US Patent Application 20040063719, Queen's University at Kingston and Callegy Pharmaceuticals Applicants; Fox DNA and Hughes B, US Patent Applications 20040077624 and 20040132731; Hepworth D, US Patent Application 20040180958, Pfizer Applicant; Kalvinish I et. al. US Patent Application 20040242590; US Patent Applications 20030225060, 20040097546, 20040204398, and 20040266821, Merck Applicant; Thomas T N, US Patent Application 20050009835; Bictash M N et. al., US Patent Application 20050049255, Pfizer Applicant; Chiang P et. al. US Patent Applications 20030125334, 20050020604, 20050032809, and 20050054656, Pfizer Applicant; Santel D J, US Patent Application 20050101608; and Ghofrani A, US Patent Application 20050107394.

Additionally disclosed uses for Compound 1 include methods of treating males with low sperm count to promote fertilization of an ovum; combinations with additional agents to treat hyperglycemia, hyperinsulinaemia, hyperlipidaemia, hypertriglyceridemia, diabetes, insulin resistance, impaired glucose metabolism, conditions of impaired glucose tolerance (IGT), conditions of impaired fasting plasma glucose, obesity, diabetic retinopathy, diabetic nephropathy, glomerulosclerosis, diabetic neuropathy, syndrome X, coronary heart disease, angina pectoris, vascular restenosis, and endothelial dysfunction; methods of reducing insulin resistance and preventing ischemia/reperfusion injury; combinations with other agents to treat depression, epilepsy, faintness attacks, hypokinesia, cranial disorders, neurodegenerative disorders, anxiety, panic, pain, irritable bowel syndrome, sleep disorders, osteoarthritis, rheumatoid arthritis, neuropathological disorders, visceral pain, functional bowel disorders, inflammatory bowel diseases, pain associated with dysmenorrhea, pelvic pain, cystitis, pancreatitis, cyclical oedema, Menires disease, hyperaldosteroneism (primary and secondary), hypercalciuria and lower urinary tract symptoms, other than urinary incontinence, associated with overactive bladder and/or benign prostatic hyperplasia; methods for stimulating ovarian follicular growth, for preventing or treating a condition involving fibrosis, and for alleviating pain or spasticity in a patient suffering from spinal cord injury. Quay S C, World Patent Application WO2004069167, Nastech Applicant; Cohen D S, US Patent Application 20030139429; Lautt W W and Macedo P, US Patent Application 20030181461; Kukreja R, US Patent Application 20040009957; Patrick J and Davis M, US Patent Application 20050143314; Nonaka S and Maruyama T, US Patent Application 20040082653; Rawson D J, US Patent Application 20040132801, Warner-Lambert Applicant; Dack K N et. al., US Patent Application 20040138274, Warner-Lambert Applicant; Field M J and Williams R G, US Patent Applications 20040092522 and 20040157847, Warner-Lambert Applicant; Westbrook S L and Zanzinger J F, US Patent Application 20040167095; Taylor C P Jr et. al., US Patent Application 20040180958, Warner-Lambert Applicant; Burgess G M, US Patent Application 20040186046, Pfizer Applicant; Palmer S S et. al. US Patent Application 20040259792; Lautt W W, US Patent Application 20050049293; Gonzalez-Cadavid, N F and Rajfer J, US Patent Application 20050085486; Takasaka S, US Patent Application 20050107405, Warner-Lambert Applicant; and Lautt W W and Macedo P, US Patent Application 20050119272, DiaMedica Applicant.

Compound 1 has been characterized by in vitro inhibition studies of human cyclic guanosine monophosphate-specific phosphodiesterases and has been demonstrated to have high potency and selectivity for the type 5 isoform over other human phosphodiesterases. In cultured rat aortic smooth muscle cells, Compound 1 dose-dependently increases intracellular concentrations of cGMP. For example, see Porst H, Int. J. Impot. Res. 2002 14(Suppl 1): S57; Daugan A et. al. J. Med. Chem. 2003 46: 4533; Daugan A C-M and Gellibert F, U.S. Pat. No. 6,143,746 to ICOS. PDE subtype selectivity is believed to be clinically important due to the potential for side effects associated with inhibition of other PDEs. For instance, inhibition of the PDE6 and possibly PDE1 subtypes are believed to cause the flushing, disrupted color vision and headaches clinically associated with less selective inhibitors (see, for instance, Bischoff E, Int. J. Impot. Res. 2004 16(Suppl. 1): S11; Kuan J and Brock G, Expert Opin. Investig. Drugs 2002 11: 1605).

Compound 1 has also been characterized in the spontaneous rat hypertension model as causing significant and long-lived blood pressure reduction following oral dosing. See e.g. Daugan A et. al., J. Med. Chem. 2003 46: 4533.

In multiple human clinical studies in males with mild to severe erectile dysfunction, treatment with Compound 1 resulted in highly significant patient-reported increases in penetration ability and ability to maintain erection during intercourse versus treatment with placebo. These benefits were observed in a wide cross section of patients including those suffering from spinal cord injuries or diabetes. See, e.g. Giuliano F et. al. Eur. Urol. 2000 37(Suppl. 2): Abst. 320; Bella A J and Brock G B, Curr. Urol. Rep. 2003 4: 472; Del Popolo G et. al. Spinal Cord. 2004 42: 643; Fonseca V et. al., Diabetologia 2004 47: 1914. Studies comparing patient preferences between Compound 1 and another commercial PDE5 inhibitor have consistently indicated a statistically significant preference for Compound 1, which has been suggested to be due to the longer pharmacological half life of Compound 1 providing a greater window of opportunity for sexual spontaneity. See Doggrell S A, Expert Opin. Pharmacother. 2005 6: 75; Stroberg P et. al., Clin. Ther. 2003 25: 2724; Govier F, Clin. Ther. 2003 25: 2709; Porst H, Int. J. Impot. Res. 2002 14(Suppl. 1): S57.

Following oral administration to humans, Compound 1 is well absorbed, followed by extensive oxidative and phase II metabolism with only a minor amount of Compound 1 being excreted unchanged (FDA NDA no. 02368, label approved on Mar. 31, 2005). The major metabolic pathway proceeds by initial oxidative cleavage of the benzodioxol ring to forming a catechol metabolite. Subsequent phase II metabolism ensues, including mainly methylation and glucuronidation; see Scheme I. In vitro measurements indicate that these metabolites do not contribute to the clinical activity of Compound 1. When Compound 1 is dosed concurrently with inhibitors of cytochrome 3A4 (CYP3A4), clinically meaningful increases in the half-life and exposure of Compound 1 measured as area under the plasma-time concentration curve (AUC) occur, leading to lower labeled dosing recommendations in patients taking such medications.

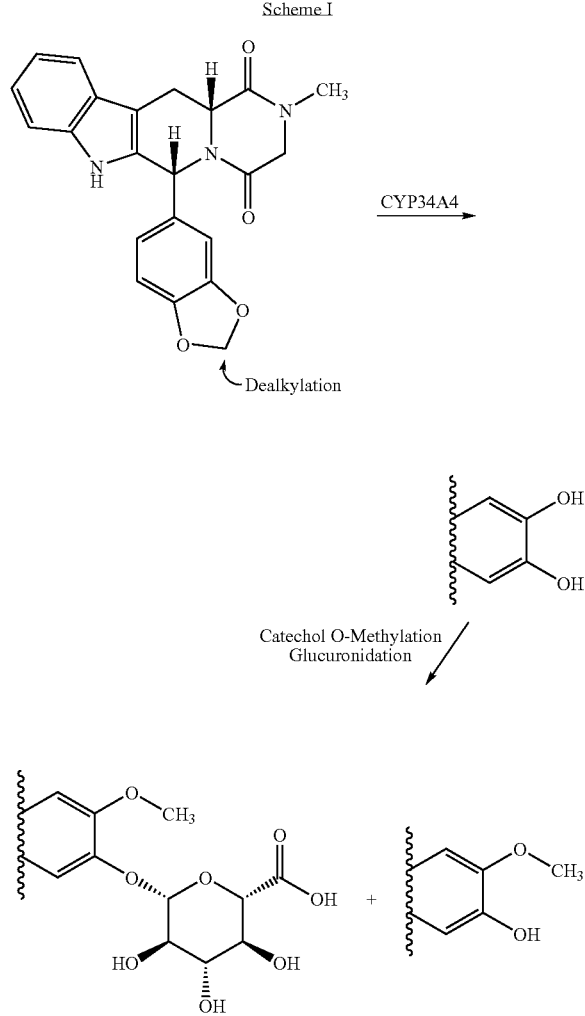

Burgess G M et. al., US Patent Application 20040186046, Pfizer Inc. Applicant ("the '046 application"), discloses PDE5 inhibitors, including Compound 1, and all isotopic variants thereof, as being useful to treat diabetes. The '046 application suggests that substitution of PDE5 inhibitors with isotopes, such as deuterium, may afford certain therapeutic advantages resulting from greater metabolic stability, such as increased in vivo half-life or reduced dosage requirements. The '046 application does not teach which PDE5 inhibitors, nor what portion of any particular PDE5 inhibitor, should be substituted with isotopes in order to produce greater metabolic stability.

It is therefore desirable to create a compound displaying the beneficial activities of Compound 1, but with a reduced rate of metabolism to further extend its pharmacological effective life.

SUMMARY OF THE INVENTION

The present invention solves the problems set forth above by providing a compound of Formula II:

or a prodrug or a prodrug salt thereof, or a solvate or polymorph of the foregoing, wherein:

$X^1$ and $X^2$ are simultaneously fluoro; or $X^1$ is deuterium and $X^2$ is selected from hydrogen or deuterium;

each Y is independently selected from deuterium or hydrogen;

the hydrogen attached to the indole nitrogen is optionally replaced by deuterium; and each carbon is independently optionally replaced by $^{13}C$.

In one embodiment, $X^1$ and $X^2$ are simultaneously hydrogen, producing a compound of Formula IIII:

In one preferred embodiment of Formula III, the compound has the formula:

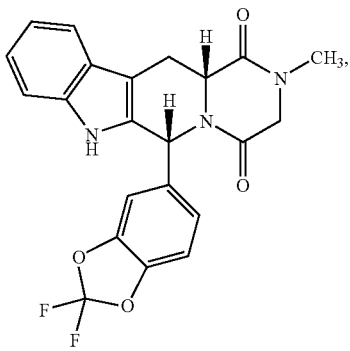

(Compound 2)

or a prodrug or a prodrug salt thereof, or a solvate, hydrate or polymorph of the foregoing, wherein the naturally abundant hydrogen attached to the indole nitrogen is not replaced by deuterium and wherein no naturally abundant carbon atoms are replaced by $^{13}C$.

In another preferred embodiment of Formula III, at least one Y is deuterium.

In another embodiment, $X^1$ is deuterium and $X^2$ is hydrogen or deuterium, resulting in a compound of the formula:

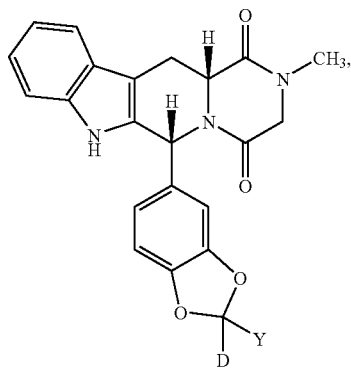

(IV)

or a prodrug or prodrug salt thereof; or a hydrate, solvate or polymorph thereof; wherein:

D is deuterium; Y is deuterium or hydrogen; each hydrogen is optionally and independently replaced with deuterium and each carbon is optionally and independently replaced with $^{13}C$.

A preferred embodiment of formula IV is a compound wherein Y is deuterium.

Another preferred embodiment is prodrug salt of a compound of formula IV wherein the counterion of the saltable prodrug is pharmaceutically acceptable.

The compounds of Formulae II, III and IV possess both altered physicochemical properties and great stability to benzodioxol ring cleavage by CYP3A4 due to the presence of fluorine and, in the case of deuterium-containing compounds of Formulae II, III and IV, replacement of hydrogen by deuterium. These novel compounds thus have beneficially enhanced pharmacological effects as compared to Compound 1. Compounds of Formulae II, III and IV, and compositions comprising them, are useful to reduce or ameliorate the severity, duration, or progression, or enhance function compromised by a disorder beneficially treated by inhibiting PDE5, or by increasing intracellular cGMP concentrations. Preferred applications for compounds of Formulae II, III and IV include methods of use in treating sexual disorders, more preferably erectile dysfunction and female arousal disorder; and cardiovascular disorders.

Fluorination has unpredictable effects on the biological activity of compounds in which it is incorporated in place of hydrogen; see e.g. Smart B E, J. Fluorine Chem. 2001 109: 3 and Ismail F M D, J. Fluorine Chem. 2002 118: 27. This is due to the exceedingly high electronegativity of fluorine relative to hydrogen, and the significantly larger van der Waals volume of fluorine in a C—F bond relative to hydrogen in a C—H bond.

2,2-Difluorinated benzodioxols are known and have been incorporated into bioactive agents, but to date are not constituents in any human drugs of which applicant is aware. See for instance Shimizu M and Hiyama T, Angew. Chem. Intl. Ed. 2005 44: 214. Their synthetic manipulation is known (e.g. see Schlosser M et. al. Eur. J. Org. Chem. 2003: 452) but the majority of known 2,2-difluorobenzodioxols possess electron-withdrawing substituents which serve to stabilize the difluoromethylenedioxy ring to hydrolytic cleavage. Indeed, in some cases 2,2-difluorobenzodioxols bearing even mildly electron donating substituents such as alkyl groups are known to resist purification by standard silica gel chromatography due to their extreme instability; see e.g. Kuroboshi M and Hiyama T, Synlett 1994: 251.

Surprisingly, a fluorine-containing compound of Formula II or III is sufficiently stable to allow ready synthetic access. It also beneficially retains high affinity for PDE5, as well as substantial separation of that activity from inhibition of other PDE enzymes, in particular PDE1 and PDE6, and actively increases intracellular cGMP in arterial and corpus cavernosum smooth muscle.

Incorporation of deuterium in place of hydrogen is known to produce significant effects on the physiological and pharmacological activities of the substituted compound. For instance, N-nitrosamines substituted with deuterium can display increased, decreased, or unchanged carcinogenicity depending on where in the compound hydrogen is replaced with deuterium and on the identity of the compound to which substitutions are made (Lijinsky W et. al. Food Cosmet. Toxicol. 1982 20: 393; Lijinsky W et. al. JCNI 1982 69: 1127). Similarly, both increases and decreases in bacterial mutagenicity of deuterium-substituted aza-amino acids are known, depending on the identity of the amino acid derivative and position of substitution (Mangold J B et. al. Mutation Res. 1994 308: 33). Reduced hepatotoxicity of certain deuterium-substituted compounds is known (Gordon W P et. al. Drug Metab. Dispos. 1987 15: 589; Thompson D C et. al. Chem. Biol. Interact. 1996 101: 1). Deuterium substitution can affect compound's odors (Turin L, Chem. Senses 1996 21: 773) and plasma protein binding (Echmann M L et. al. J. Pharm. Sci. 1962 51: 66; Cherrah Y. et. al. Biomed. Environm. Mass Spectrom. 1987 14: 653; Cherrah Y. et. al. Biochem. Pharmacol. 1988 37: 1311). Changes in the biodistribution and clearance of certain deuterium-substituted compounds suggests changes in their recognition by active transport mechanisms (Zello G A et. al. Metabolism 1994 43: 487; Gately S J et. al. J. Nucl. Med. 1986 27: 388; Wade D, Chem. Biol. Interact. 1999 117: 191).

Replacement of hydrogen with deuterium at sites subject to oxidative metabolism by, for instance, heme proteins such as cytochrome P450 and peroxidase enzymes, is known in certain, but not all, cases to produce a significant reduction in the rate of metabolism due to the primary isotope effect of breaking the C—$^1$H versus C—$^2$H bond (see, e.g., Guengerich F P et. al. J. Biol. Chem. 2002 277: 33711; Kraus, J A and Guengerich, F P, J. Biol. Chem. 2005 280: 19496; Mitchell K H et. al., Proc. Natl. Acad. Sci. USA 2003 109: 3784; Nelson S D and Trager W F, Drug Metab. Dispos. 2003 31: 1481; Hall L R and Hanzlik, R P J. Biol. Chem. 1990 265: 12349; Okazaki O. and Guengerich F P J. Biol. Chem. 268, 1546; Iwamura S et. al. J. Pharmacobio-Dyn. 1987 10: 229). If the C—H bond breaking step is rate-limiting a substantial isotope effect can be observed. If other steps determine the overall rate of reaction, the isotope effect may be insubstantial. In cases where a rate limiting step of a reaction involves rehybridization of the attached carbon from sp2 to sp3, deuterium substitution often creates a negative isotope effect, speeding up the reaction rate. Introducing deuterium into a compound at a site subject to enzymatic oxidation does not predictably produce a significant pharmacokinetic change. See for instance Mamada K et. al. Drug Metab. Dispos. 1986 14: 509; Streeter A J et. al. Arch. Toxicol. 1990 64: 109; Morgan D S et. al., Int. Arch. Occup. Environ. Health 1993 65(1 Suppl.): S139.

Although incorporation of deuterium into specific organic compounds can change their pharmacological properties, general exposure to and incorporation of deuterium is safe within levels potentially achieved by use of compounds of this invention as medicaments. For instance, the weight percentage of hydrogen in a mammal (approximately was 9%) and natural abundance of deuterium (approximately 0.015%) indicates, for instance, that an average adult US male normally contains approximately 1.2 grams of deuterium (see e.g. Harper V W et. al. *"Review of Physiological Chemistry"* 16$^{th}$ Edition, 1977, Lange Medical Publications; Ogden C L et. al. CDC Adv. Data 2004 347: 1; www.cdc.gov/nchs/data/ad/ad347.pdf). Furthermore, replacement of up to about 15% of normal hydrogen with deuterium has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. N.Y. Acad. Sci 1960 84: 736; Czakja D M et. al., Am. J. Physiol. 1961 201: 357). Higher deuterium concentrations, usually in excess of 20%, can be toxic in animals. However, acute replacement of as high as 15%-23% of the hydrogen in humans' fluids with deuterium was found not to cause toxicity (Blagojevic N et. al. in *"Dosimetry & Treatment Planning for Neutron Capture Therapy"*, Zamenhof R, Solares G and Harling O Eds. 1994. Advanced Medical Publishing, Madison Wis. pp. 125-134.). These authors report a clinical protocol in their practice involving oral administration of up to 1 liter per day of deuterated water ($D_2O$) for up to 5 days, followed by intravenous administration of 4 liters of deuterated water prior to radiation procedures; this deuterated water is readily incorporated throughout the body beyond the fluid compartment, including in glucose and glycogen, fats, and cholesterol and thus cell walls (e.g. see Diabetes Metab. 1997 23: 251). In a 70 kg human male, 15% replacement of the hydrogen in the fluid compartment with deuterium corresponds to incorporation of approximately 1 kg of deuterium or the equivalent of approximately 5 kg of deuterated water. These quantities are orders of magnitude beyond the conceived level of administration of any of the deuterium-containing compounds of this invention.

Deuterium tracers including deuterium-labeled drugs and doses, in some cases repeatedly, of thousands to tens of thousands of milligrams of deuterated water, are also used in healthy humans of all ages including neonates and pregnant women, without reported incident (e.g. Pons G and Rey E, Pediatrics 1999 104: 633; Coward W A et. al., Lancet 1979 7: 13; Schwarcz H P, Control. Clin. Trials 1984 5(4 Suppl): 573; Eckhardt C L et. al. Obes. Res. 2003 11: 1553; Rodewald L E et. al., J. Pediatr. 1989 114: 885; Butte N F et. al. Br. J. Nutr. 1991 65: 3; MacLennan A H et. al., Am. J. Obstet. Gynecol. 1981 139: 948). Thus, it is clear that any deuterium released, for instance, during the metabolism of the deuterium-containing compounds of this invention poses no health risk.

The compounds of this invention display reduced rates of oxidative metabolism as compared with the medically important Compound 1. This is expected to further extend the pharmacological lifetime of a therapeutic dose of compounds of this invention with respect to a similar dose of Compound 1, beneficially extending the patient's window of opportunity for sexual spontaneity.

The altered properties of the isotopically modified compounds of this invention will not obliterate their ability to bind to their protein target. This is because such binding is primarily dependent upon non-covalent binding between the protein and the inhibitor which may be impacted both positively and negatively by isotopic substitution, depending on the specific substitution involved, and any negative effects that a heavy atom of this invention may have on the highly optimized non-covalent binding between compounds of formula I and serotonin uptake proteins will be relatively minor. Major factors contributing to the noncovalent recognition of small molecules by proteins and the binding strength between them include: Van der Waals forces, hydrogen bonds, ionic bonds, molecular reorganization, desolvation energy of the small molecule, hydrophobic interactions and, in certain instances, displacement energy for pre-existing bound ligands. See, for instance, Goodman & Gilman's *The Pharmacological Basis of Therapeutics*, Tenth Edition, Hardman J G and Limbird L E, eds. McGraw-Hill, 2001 and *The Organic Chemistry of Drug Design and Drug Action*, Silverman R B, 2004, Academic Press.

The compounds of this invention possess molecular topology that is well within the conformational envelope encompassed by the known active compounds of Formula I. The replacement of hydrogen by deuterium does not alter molecular shape and exchange of $^{13}$C for $^{12}$C is conformationally neutral (Holtzer M E et. al., Biophys. J. 2001 80: 939). Deuterium replacement does cause a slight decrease in Van der Waals radius (Wade D, Chem. Biol. Interact. 1999 117: 191); but applicant believes that such decrease will not greatly reduce binding affinity between the molecule and its receptor. Furthermore, the smaller size of the deuterated compounds prevents their being involved in new undesirable steric clashes with the binding protein relative to the Compound 1. Neither deuterium nor $^{13}$C atoms in the compounds of this invention contribute significantly to hydrogen bonding or ionic interactions with the protein receptors. This is because the major hydrogen bond and ionic interactions formed by Compound 1 with PDE5 are mediated by the nitrogens and oxygens within Compound 1 and possibly its indole NH proton acting as a hydrogen bond donor. Any deuterium atoms attached to the indole nitrogen will be rapidly exchanged with bulk solvent protons under physiological conditions. Protein reorganization or side chain movement will be identical between a compound of this invention and their light atom isotopologues. Desolvation energy of a compound of this invention will be equivalent to or less than that of Compound 1, resulting in neutral or increased binding affinity for the receptor; Turowski M et. al., J. Am. Chem. Soc. 2003 125: 13836. The replacement of $^{13}$C in place of $^{12}$C in compounds of this invention will have no practical change in desolvation.

DETAILED DESCRIPTION OF THE INVENTION

The present invention provides a compound of Formula II:

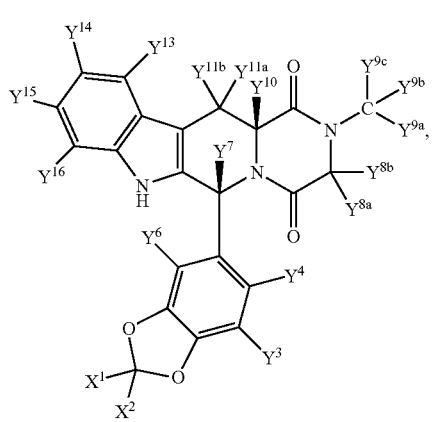

(II)

wherein:

$X^1$ and $X^2$ are simultaneously fluoro; or $X^1$ is deuterium and $X^2$ is selected from hydrogen or deuterium;

each Y is independently selected from deuterium or hydrogen;

the hydrogen attached to the indole nitrogen is optionally replaced by deuterium; and each carbon is independently optionally replaced by $^{13}C$.

In one preferred embodiment of Formula II, at least one Y is deuterium. More preferably one or more of $Y^4$, $Y^7$ $Y^{8a}$, $Y^{8b}$, $Y^{9a}$, $Y^{9b}$ or, $Y^{9c}$ are deuterium. Even more preferred embodiments are a compound wherein $Y^4$ is deuterium, a compound wherein $Y^7$ is deuterium, a compound wherein $Y^{8a}$ and $Y^{8b}$ are both deuterium, a compound wherein each of $Y^{9a}$, $Y^{9b}$ and, $Y^{9c}$ are deuterium; and a compound combining one or more of the foregoing deuterium substitutions.

In each of the preferred compounds set forth above, it is further preferred that all hydrogen atoms not specifically replaced with deuterium and all carbon atoms not specifically replaced with $^{13}C$ are present at their natural isotopic abundance. Throughout this specification, reference to "each Y" includes, independently, all "Y" groups including for example $Y^3$, $Y^4$, $Y^6$, $Y^7$, $Y^8$, $Y^{8a}$, $Y^{8b}$, $Y^9$, $Y^{9a}$, $Y^{9b}$, $Y^{9c}$, $Y^{10}$, $Y^{11}$, $Y^{11a}$, $Y^{11b}$, $Y^{13}$, $Y^{14}$, $Y^{15}$, $Y^{16}$, where applicable.

In one preferred embodiment, the invention provides a compound wherein $X^1$ and $X^2$ are simultaneously fluoro:

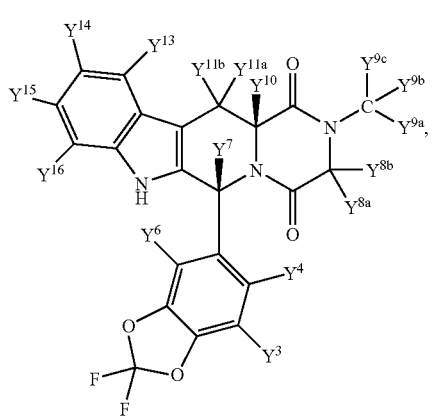

(III)

or a prodrug or a prodrug salt thereof, or a solvates or polymorph of the foregoing.

In a preferred embodiment of Formula III, the compound has the formula:

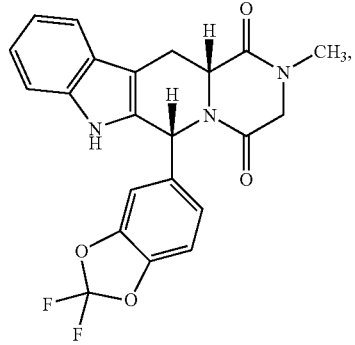

(Compound 2)

or a prodrug or a prodrug salt thereof, or a solvate, hydrate or polymorph of the foregoing, wherein the hydrogen attached to the indole nitrogen is not replaced by deuterium and wherein no carbon atoms are replaced by $^{13}C$.

In another preferred embodiment, the invention provides a compound wherein $X^1$ is deuterium and $X^2$ is selected from hydrogen or deuterium:

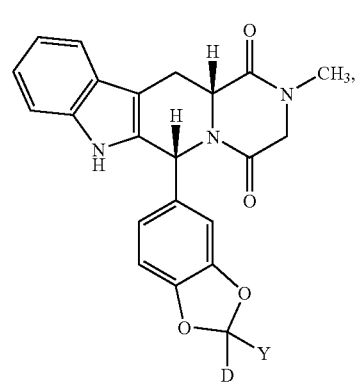

(IV)

or a prodrug or prodrug salt thereof; or a hydrate, solvate or polymorph thereof; wherein: D is deuterium; Y is deuterium or hydrogen; each hydrogen is optionally and independently replaced with deuterium; and each carbon is optionally and independently replaced with $^{13}C$.

According to a preferred embodiment of Formula IV, Y is deuterium. Even more preferred is when up to three additional hydrogen atoms are replaced by deuterium.

According to another preferred embodiment of Formula IV, one carbon atom is replaced by $^{13}C$.

The term "compound" as used herein, is intended to include prodrugs and prodrug salts of a compound of this invention. The term also includes any solvates, hydrates and polymorphs of any of the foregoing. The specific recitation of "prodrug," "prodrug salt," "solvate," "hydrate," or "polymorph" in certain aspects of the invention described in this application shall not be interpreted as an intended omission of these forms in other aspects of the invention where the term "compound" is used without recitation of these other forms.

As used herein and unless otherwise indicated, the term "prodrug" means a derivative of a compound that can hydrolyze, oxidize, or otherwise react under biological conditions (in vitro or in vivo) to provide a compound of this invention. Prodrugs may only become active upon such reaction under biological conditions, or they may have activity in their unreacted forms. Examples of prodrugs contemplated in this invention include, but are not limited to, analogs or derivatives of compounds of any one of the formulae disclosed herein that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of compounds of any one of the formulae disclosed herein that comprise —NO, —NO$_2$, —ONO, or —ONO$_2$ moieties. Prodrugs can typically be prepared using well-known methods, such as those described by Burger's Medicinal Chemistry and Drug Discovery (1995) 172-178, 949-982 (Manfred E. Wolff ed., 5th ed); see also Goodman and Gilman's, The Pharmacological basis of Therapeutics, 8th ed., McGraw-Hill, Int. Ed. 1992, "Biotransformation of Drugs".

As used herein and unless otherwise indicated, the terms "biohydrolyzable amide", "biohydrolyzable ester", "biohydrolyzable carbamate", "biohydrolyzable carbonate", "biohydrolyzable ureide" and "biohydrolyzable phosphate analogue" mean an amide, ester, carbamate, carbonate, ureide, or phosphate analogue, respectively, that either: 1) does not destroy the biological activity of the compound and confers upon that compound advantageous properties in vivo, such as uptake, duration of action, or onset of action; or 2) is itself biologically inactive but is converted in vivo to a biologically active compound. Examples of biohydrolyzable amides include, but are not limited to, lower alkyl amides, α-amino acid amides, alkoxyacyl amides, and alkylaminoalkylcarbonyl amides. Examples of biohydrolyzable esters include, but are not limited to, lower alkyl esters, alkoxyacyloxy esters, alkyl acylamino alkyl esters, and choline esters. Examples of biohydrolyzable carbamates include, but are not limited to, lower alkylamines, substituted ethylenediamines, amino acids, hydroxyalkylamines, heterocyclic and heteroaromatic amines, and polyether amines.

A prodrug salt is a compound formed between an acid and a basic group of the prodrug, such as an amino functional group, or a base and an acidic group of the prodrug, such as a carboxyl functional group. In a preferred embodiment, the prodrug salt is a pharmaceutically acceptable salt. According to another preferred embodiment, the counterion to the saltable prodrug of the compound of formula I is pharmaceutically acceptable. Pharmaceutically acceptable counterions include, for instance, those acids and bases noted herein as being suitable to form pharmaceutically acceptable salts.

Particularly favored prodrugs and prodrug salts are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or central nervous system) relative to the parent species. Preferred prodrugs include derivatives where a group that enhances aqueous solubility or active transport through the gut membrane is appended to the structure of formulae described herein. See, e.g., Alexander, J. et al. Journal of Medicinal Chemistry 1988, 31, 318-322; Bundgaard, H. Design of Prodrugs; Elsevier: Amsterdam, 1985; pp 1-92; Bundgaard, H.; Nielsen, N. M. Journal of Medicinal Chemistry 1987, 30, 451-454; Bundgaard, H. A Textbook of Drug Design and Development; Harwood Academic Publ.: Switzerland, 1991; pp 113-191; Digenis, G. A. et al. Handbook of Experimental Pharmacology 1975, 28, 86-112; Friis, G. J.; Bundgaard, H. A Textbook of Drug Design and Development; 2 ed.; Overseas Publ.: Amsterdam, 1996; pp 351-385; Pitman, I. H. Medicinal Research Reviews 1981, 1, 189-214.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound or a prodrug of a compound of this invention. A "pharmaceutically acceptable counterion" is an ionic portion of a salt that is not toxic when released from the salt upon administration to a recipient.

Acids commonly employed to form pharmaceutically acceptable salts include inorganic acids such as hydrogen bisulfide, hydrochloric, hydrobromic, hydroiodic, sulfuric and phosphoric acid, as well as organic acids such as para-toluenesulfonic, salicylic, tartaric, bitartaric, ascorbic, maleic, besylic, fumaric, gluconic, glucaronic, formic, glutamic, methanesulfonic, ethanesulfonic, benzenesulfonic, lactic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephathalate, sulfonate, xylenesulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and the like salts. Preferred pharmaceutically acceptable acid addition salts include those formed with mineral acids such as hydrochloric acid and hydrobromic acid, and especially those formed with organic acids such as maleic acid.

Suitable bases for forming pharmaceutically acceptable salts with acidic functional groups of prodrugs of this invention include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl, N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N,-di-lower alkyl-N-(hydroxy lower alkyl)-amines, such as N,N-dimethyl-N-(2-hydroxyethyl)amine, or tri-(2-hydroxyethyl)amine; N-methyl-D-glucamine; and amino acids such as arginine, lysine, and the like.

As used herein, the term "hydrate" means a compound which further includes a stoichiometric or non-stoichiometric amount of water bound by non-covalent intermolecular forces.

The term "solvate" means a compound which further includes a stoichiometric or non-stoichiometric amount of solvent such as water, acetone, ethanol, methanol, dichloromethane, 2-propanol, or the like, bound by non-covalent intermolecular forces.

As used herein, the term "polymorph" means solid crystalline forms of a compound or complex thereof. Different polymorphs of the same compound can exhibit different physical, chemical and/or spectroscopic properties. Different physical properties include, but are not limited to stability (e.g., to heat, light or moisture), compressibility and density (important in formulation and product manufacturing), hygroscopicity, solubility, and dissolution rates (which can affect bioavailability). Differences in stability can result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to thermodynamically more stable polymorph) or both (e.g., tablets of one polymorph are more susceptible to breakdown at high humidity). Different physical properties of polymorphs can affect their processing. For example, one polymorph might be more likely to form solvates or might be more difficult to filter or wash free of impurities than another due to, for example, the shape or size distribution of particles of it.

The compounds of the present invention contain asymmetric carbon atoms. As such, a compound of this invention can exist as an individual stereoisomer as well as a mixture of stereoisomers. Accordingly, a compound of the present invention will include not only a stereoisomeric mixture, but also individual respective stereoisomers substantially free from other stereoisomers. The term "substantially free" as used herein means less than 25% of other stereoisomers, preferably less than 10% of other stereoisomers, more preferably less than 5% of other stereoisomers and most preferably less than 2% of other stereoisomers, are present. Methods of obtaining or synthesizing stereoisomers are well known in the art and may be applied as practicable to final compounds or to starting material or intermediates. In another embodiment, the compound is an isolated compound.

The compounds of the invention may be synthesized by well-known techniques. The starting materials and certain intermediates used in the synthesis of the compounds of this invention are available from commercial sources or may themselves be synthesized using reagents and techniques known in the art, including those synthesis schemes delineated herein. See, for instance, Daugan A C-M, U.S. Pat. No. 5,859,006, Assigned to ICOS Corporation; Daugan A C-M, U.S. Pat. No. 6,140,329, Assigned to ICOS Corporation; Daugan A C-M and Gellibert F, U.S. Pat. No. 6,143,746, Assigned to ICOS Corporation; and Daugan A C-M et. al., J. Med. Chem. 2003 46: 4533. Each of these documents is incorporated herein by reference.

Scheme II

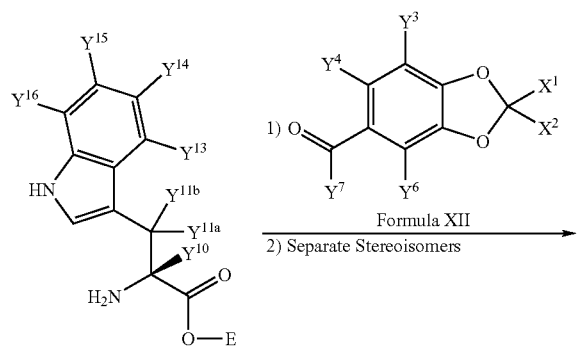

Formula XII

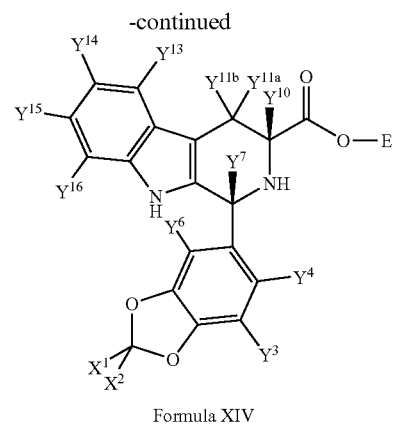

Formula XIV

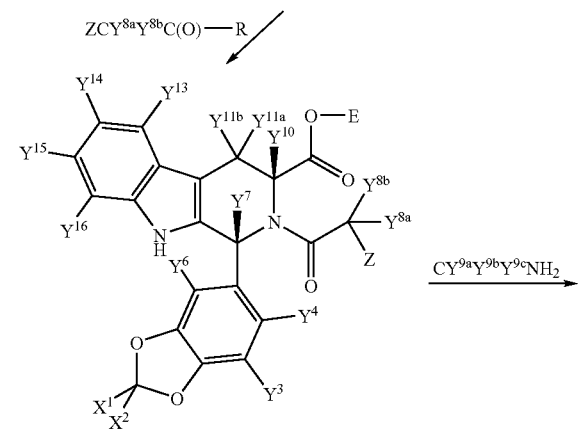

Formula XV

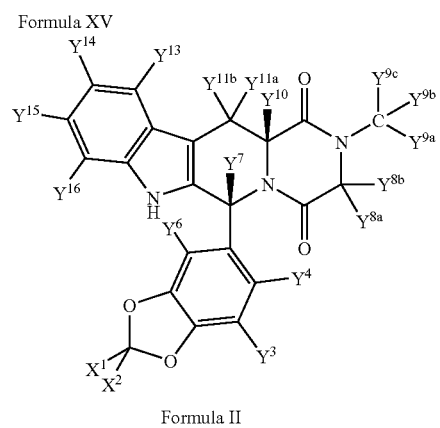

Formula II

A convenient method for producing compounds of Formula II is shown graphically in Scheme II. In Scheme II, E represents a functional group that is known in the art of organic synthesis as an ester group, or functional equivalent, labile to ring closure during the formation of cyclic amides. Suitable E groups include, for instance, methyl, ethyl, propyl, butyl, isobutyl, cyclopropylethyl, phenyl, benzyl, 4-chlorobenzyl, 2-nitrobenzyl, allyl, propargyl, trichloroethyl, and so forth. Many such additional suitable groups will be evident to those of skill in the art; for instance, certain amides can also be in such cyclization reactions. Preferred E groups include methyl, ethyl, benzyl, allyl, and most preferably, methyl. Each Y is independently hydrogen or deuterium. $X^1$ and $X^2$ are simultaneously fluoro; or $X^1$ is deuterium and $X^2$ is selected from hydrogen or deuterium. Z represents a leaving group such as are known in the art, many of which will be apparent to the skilled artesian. Preferred Z groups include halides such as chloride, bromide, and iodide; and sulfonates such as tosylate, mesylate, brosylate, nosylate, and the like. Chloride and bromide are more preferred. R represents an acid activating group such as are known in the art, including halide such as fluoride, chloride and bromide; anhydrides such as symmetrical anhydrides, pivalic anhydride, and other mixed anhydrides such as those formed upon reaction with chloroformates; activated esters such as pentafluoromethyl, succinimidyl, and the like. Other hydrogen and carbon atoms in compounds of formulae II, XIII, XIV and XV are optionally replaced with deuterium and $^{13}C$, respectively. Modifications of the above scheme will be apparent to those of skill in the art of organic synthesis.

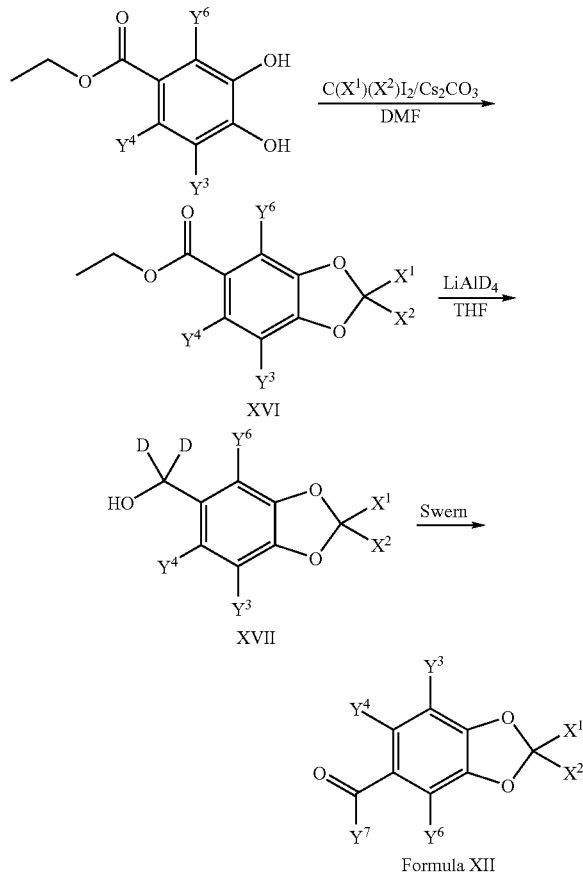

The synthesis of compounds of formula XII is demonstrated in Scheme III. A di-hydroxy phenyl ring is alkylated with an alkylating agent $CX^1X^2I_2$ (e.g., dideutero-diiodomethane), to form a compound of formula XVI. The ester group is reduced in the presence of $LiAlD_4$ to form a compound of formula XVII, which is subsequently oxidized (e.g., under Swern conditions) to form the starting compound of formula XII. The definitions of Y and X are as defined herein.

Deuterated and $^{13}C$-substituted indole, D,L-tryptophan, haloacetates such as chloroacetic acid and chloracetyl chloride, and glycine derivatives, are commercially available (e.g. C/D/N Isotopes, Pointe-Claire, Quebec, Canada; Sigma Aldrich (ISOTEC), St. Louis, Mo.) and allow synthesis of the correspondingly labeled tryptophan derivatives and acetyl-labeled compounds of formula XIV by means known in the art of organic and biochemical synthesis. For instance, see Greenstein J P, Methods Enzymol. 1957 3: 554; Stewart K K and Doherty R F, Proc. Natl. Acad. Sci. USA 1973 70: 2850; Venkatachalam S et. al., Org. Prep. Proc. Intl. 1993 25: 249; Evans D A et. al., in *Peptides, Chemistry and Biology*, Marshall G R (Ed.) 1999 Escom, Leiden, Holland p. 143; Evans D A et. al., J. Am. Chem. Soc. 1990 112: 4011; Schollkopf U, Pure Appl. Chem. 1983 55: 1799; Myers A G and Gleason J L, Org. Synth. 1999 76: 57; Watanabe T and Snell E E, Proc. Natl. Acad. Sci USA 1972 69: 1086; and Xiong C et. al. J. Org. Chem. 2002 22: 1399.

Fluorinated compounds of Formula III can be readily synthesized by the skilled chemist. For instance, (3,4-difluoromethylenedioxy)bromobenzene (also known as 5-bromo-2,2-difluorobenzo[d][1,3]dioxole) can be obtained as an item of commerce or prepared as described by Benefiel R L and Krumkalns E V, U.S. Pat. No. 4,110,099 to Eli Lilly. Metal-halogen exchange followed by reaction with a formylating reagent such as, for instance, dimethylformamide yields the compound of Formula III. Heavy atom isotopologues of Formula III are also available by means known in the art of organic synthesis. For instance, reaction of the aforementioned organometallic reagent with commercially available deuterated or $^{13}C$ formyl-substituted dimethylformamide yields isotopologues bearing heavy atoms at the formyl group. Reaction of 3,4-dihydroxybromobenzene with $^{13}C$-labled methylene chloride by means known in the art (e.g. Cabedo N et. al., J. Med. Chem. 2001 44: 1794; Panseri P et. al. U.S. Pat. No. 5,936,103 to Borregaard Italia), followed by conversion of the resulting (3,4-methylene-$^{13}C$-dioxy)bromobenzene to its difluoromethylene analog (e.g. U.S. Pat. No. 4,110,099) and formylation installs $^{13}C$ in the methylene carbon of Formula III. Analogous methylene fluorination of the commercial 5,6-dibromobenzo[d][1,3]dioxole, available e.g. from Chemos GmbH, Regenstauf, Germany as 1,2-dibromo-4,5-methylenedioxy-benzene, followed by reaction with one equivalent of a metallating reagent such as n-butyl-lithium, and subsequent deuterium quench, yields 5-bromo-6-deutero-2,2-difluorobenzo[d][1,3]dioxole. Subsequent metallation and formylation then yields the compound of Formula III wherein $Y^4$ is deuterium. Due to the strong acidic nature of the 2,2-difluorobenzo[d][1,3]dioxole ring ortho to the oxygen atoms, essentially all substitution patterns are accessible through halogenation and lithiation, or catalytic reduction of halogens under deuterium gas by means known in the art (e.g. see Yadav J S et. al., Adv. Synth. Catal. 2004 346: 77; Kirefu T, et. al. J. Label. Compd. Radiopharm. 2001 44: 329) and removable protection as necessary. See Gorecka J et al. Eur. J. Org. Chem. 2004: 64; and Schlosser M et. al., Eur. J. Org. Chem. 2003: 452. 2,2-Difluorobenzo[d][1,3]dioxoles are also available by a different approach involving conversion of the corresponding catechols to thiocarbonates, for instance using thiophosgene, followed by reaction with a fluorinating reagent such as n-$Bu_4NH_2F_3$ and a suitable oxidant such as N-halo-succinimide or 1,3-dibromo-5,5-dimethylhydantoin (Kuroboshi M and Hiyama T, Synlett 1994 251; Cousseau J and Albert P, Bull. Chim. Soc. Fr. 1986 910).

2,2-Difluorobenzo[d][1,3]dioxole-5-carboxaldehyde and its heavy atom isotopologues may be used in place of the non-fluorinated, light atom analog (i.e. benzo[d][1,3]dioxole-5-carboxaldehyde) in any of the reaction schemes known for the synthesis of Compound 1 to produce a compound of Formula III. Due to the electron withdrawing nature of the carboxaldehyde substituent, this 1,3-benzodioxole derivative is reasonably stable to acidic conditions, but appropriate care may be helpful, for instance, in acidic condition and reaction workups to avoid any degradation of the reaction product, such as those in Pictet-Spengler reaction, if such an approach is used to produce Compound 2.

The acid cyclization catalyst can be a strong protic acid (see e.g. Whaley W M and Govindachari T R, Org. React. 1951 6: 74), or a Lewis acid or Bronsted acid-assisted Lewis acid (e.g. Yamada H et. al. J. Org. Chem. 1998 63: 6348). Many variations in this cyclization reaction, commonly referred to as the Pictet-Spengler reaction, are known, including those that enhance enantiomeric or diastereomeric excesses in the products. For instance, see Rozwadowski M D, Heterocycles 1994 39: 903; Campiglia P et. al., Mol. Divers. 2004 8: 427, Horiguchi Y et. al. Chem. Pharm. Bull. 2003 51: 1368, and Nakamura S et. al., Org. Lett. 2003 5: 2087. If the reaction is carried out in aprotic solvent with a Lewis acid, or alternatively under protic conditions wherein the acid protons have been replaced with deuterium, e.g. using $CF_3CO_2D$, then the resulting compound of formula XIV will bear a deuterium at $Y^7$.

Deuterated compounds of Formula IV can be synthesized, for instance, by reaction of 3,4-dihydroxybenzaldehyde with suitable deuterated methylenation reagents. Examples of such reagents include, for instance, mono and di-deuterated forms of dihalomethanes such as dichloromethane, dibromomethane, bromochloromethane, diiodomethane, and the like. The synthesis of benzodioxols from catechol (o-dihydroxyphenyl) precursors is well known in the art and is described, for instance by Cabedo N et. al., J. Med. Chem. 2001 44: 1794; Walz A J and Sundberg R J, J. Org. Chem., 2000 65: 8001; Orús L et. al., J. Med. Chem. 2002 45: 4128; Chang J et. al. Helv. Chim. Acta 2003 86: 2239; Moreau A et. al., Tetrahedron 2004 60: 6169; and Panseri P et. al. U.S. Pat. No. 5,936,103 to Borregaard Italia, each of which is herein incorporated by reference. The latter reference provides a particularly efficient method which for large-scale production that can be adapted to the readily available dichlorodideuteromethane.

In Scheme II, separation of the tetrahydro-β-carboline cis-trans isomers; acylation, for instance with chloroacetyl chloride; and ring closure, preferably with methylamine, is then carried out in a manner analogous to that described for the synthesis of Compound 1 in the art, such as in the above-cited references.

Deuterated, $^{13}C$-labeled methylamine is commercially available, allowing isotopic substitution of the N-methyl group attached to the dioxopiperazine ring.

By means as described above and other that will be apparent to those of skill in the art of organic synthesis, substitution of hydrogens and carbons in compounds of this invention by deuterium and $^{13}C$, respectively, may be readily accomplished.

Methods for optimizing reaction conditions, if necessary minimizing competing by-products, are known in the art. Reaction optimization and scale-up may advantageously utilize high-speed parallel synthesis equipment and computer-controlled microreactors (e.g. *Design And Optimization in Organic Synthesis, $2^{nd}$ Edition,* Carlson R, Ed, 2005; Elsevier Science Ltd.; Jähnisch, K et al, Angew. Chem. Int. Ed. Engl. 2004 43: 406; and references therein). Additional reaction schemes and protocols may be determined by the skilled artesian by use of commercially available structure-searchable database software, for instance, SciFinder® (CAS division of the American Chemical Society) and CrossFire Beilstein® (Elsevier MDL), or by appropriate keyword searching using an internet search engine such as Google® or keyword databases such as the US patent and Trademark Office text database.

The synthetic methods described herein may also additionally include steps, either before or after the steps described specifically herein, to add or remove suitable protecting groups in order to ultimately allow synthesis of the compound of the formulae described herein.

According to another embodiment, the invention provides any of above-described intermediate compounds XIV or XV, wherein at least one hydrogen or carbon atom has been substituted by deuterium or $^{13}C$, respectively. The invention also provides intermediate compound XIII, wherein one $X^1$ is deuterium and $X^2$ is selected from hydrogen or deuterium.

Combinations of substituents and variables envisioned by this invention are only those that result in the formation of stable compounds. The term "stable", as used herein, refers to compounds which possess stability sufficient to allow manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to the reduction of PDE5 activity).

The term "isotopologue" refers to species that differ from a compound of this invention only in the isotopic composition of their molecules or ions. The terms "lighter isotopologue" and "lighter atom isotopologue" as used herein, refer to species that differs from a compound of this invention in that it comprises one or more light isotopic atoms $^1H$ or $^{12}C$ at positions occupied by a deuterium or $^{13}C$. For the purposes of this invention, $^{11}C$ is not referred to as a light isotope of carbon.

A specific compound of this invention may also be referred to as a "heavy atom isotopic compound" to distinguish it from its lighter isotopologues when discussing mixtures of isotopologues. This is because a specific compound and all of its lighter isotopologues, including Compound 2 which lacks deuterium and $^{13}C$, are compounds of Formula II.

Chemical naming terminology can be complex and different chemical names can often reasonably be applied to the same structure. To avoid any confusion, "Compound 1" refers to the free base form of the active PDE5-inhibiting agent of the drug approved for sale in the US by the US FDA in NDA no. 021368.

It will be recognized that many commonly occurring atoms in biological systems exist naturally as mixtures of isotopes. Thus, any compound of Formula I inherently comprises small amounts of deuterated and/or $^{13}C$-containing isotopologues. The present invention differentiates such forms having minor amounts of such isotopologues from its scope in that the term "compound" as used in this invention refers to a composition of matter that is predominantly a specific isotopologue. A compound, as defined herein, in embodiments contains less than 10%, preferably less than 6%, and more preferably less than 3% of all other isotopologues. A compound of this invention preferably comprises hydrogen and carbon atoms, not specifically designated as deuterium and $^{13}C$, respectively, in their natural isotopic abundance. Compositions of matter that contain greater than 10% of all other specific isotopologues combined are referred to herein as mixtures and must meet the parameters set forth below. These limits of isotopic composition, and all references to isotopic composition herein, refer solely to the active form of the compound of Formula II and do not include the isotopic composition of hydrolysable portions of prodrugs, or of prodrug salt counterions, certain of which, such as chloride and bromide, exist naturally as mixtures comprising substantial percentages of multiple isotopes.

The term "heavy atom" refers to isotopes of higher atomic weight than the predominant naturally occurring isotope.

The term "stable heavy atom" refers to non-radioactive heavy atoms.

Both "$^2$H" and "D" refer to deuterium.

"Stereoisomer" refers to both enantiomers and diastereomers

"PDE" refers to cyclic guanosine monophosphate-specific phosphodiesterase

"cGMP" refers to cyclic guanosine monophosphate

"5'-GMP" refers to guanosine-5'-monophosphate

"cAMP" refers to cyclic adenosine monophosphate

"5'-AMP" refers to adenosine-5'-monophosphate

"AIBN" refers to 2,2'-azo-bis(isobutyronitrile)

"THF" refers to tetrahydrofuran

"DMF" refers to dimethylformamide

"n-BuLi" refers to 1-butyllithium

"aq." Refers to aqueous

"h" refers to hours

"min" refers to minutes

"brine" refers to saturated aqueous sodium chloride

"US" refers to the United States of America

"FDA" refers to Food and Drug Administration

"NDA" refers to New Drug Application

"AUC" refers to area under the plasma-time concentration curve

CYP3A4 refers to cytochrome P450 oxidase isoform 3A4

CYP2D6 refers to cytochrome P450 oxidase isoform 2D6

"MC-4R" refers to the human melanocortin-4 receptor

"5-HT" refers to 5-hydroxytryptamine or serotonin

"NEP" refers to neutral endopeptidase (EC 3.4.24.11)

"HMG-CoA" refers to 3-hydroxy-3-methylglutaryl-coenzyme A

"ETA" refers to endothelin subtype A receptors

"ETB" refers to endothelin subtype B receptors

"PPAR" refers to peroxisome proliferator-activated receptor.

The invention further provides compositions comprising (consisting essentially of, consisting of) a mixture of a compound of this invention and its lighter isotopologues. These mixtures may occur, for instance, simply as the result of an inefficiency of incorporating the isotope at a given position; intentional or inadvertent exchange of protons for deuterium, e.g. exchange of bulk solvent for heteroatom-attached deuterium; or intentional mixtures of pure compounds.

In one embodiment, such mixtures comprise at least about 50% of the heavy atom isotopic compound (i.e., less than about 50% of lighter isotopologues). More preferable is a mixture comprising at least 80% of the heavy atom isotopic compound. Most preferable is a mixture comprising 90% of the heavy atom isotopic compound.

In an alternate embodiment the mixture comprises a compound and its lighter isotopologues in relative proportions such that at least about 50%, preferably at least 80%, more preferably at least 90%, even more preferably at least 95% and most preferably at least 98% of the compounds in said mixture comprise an isotope at each position containing a stable heavy atom isotope in the full isotopic compound. The following exemplifies this definition. A hypothetical compound of the invention contains deuterium at positions $Y^{9a}$, $Y^{9b}$ and $Y^{9c}$. A mixture comprising this compound and all of its potential lighter isotopologues and the relative proportion of each is set forth in the table below.

TABLE 1

|  | $Y^{9a}$ | $Y^{9b}$ | $Y^{9c}$ | Relative Amt |
| --- | --- | --- | --- | --- |
| Compound | D | D | D | 40% |
| Isotopologue 1 | D | D | H | 15% |
| Isotopologue 2 | D | H | D | 14% |
| Isotopologue 3 | H | D | D | 13% |
| Isotopologue 4 | D | H | H | 6% |
| Isotopologue 5 | H | D | H | 5% |
| Isotopologue 6 | H | H | D | 4% |
| Isotopologue 7 | H | H | H | 3% |
| % of compounds comprising an isotope at position indicated position | (40% + 15% + 14% + 6%) = 75% | (40% + 15% + 13% + 5%) = 73% | (40% + 14% + 13% + 4%) = 72% |  |

From the table it can be seen that the compound plus lighter isotopologues 1, 2 and 4 comprise the isotope deuterium at position $Y^{9a}$. These compounds are present in the mixture at relevant amounts of 40%, 15%, 14% and 6%. Thus, 75% of the mixture comprises the isotope at $Y^{9a}$ that is present in the compound. The compound plus lighter isotopologues 1, 3 and 5 comprise the isotope deuterium at position $Y^{9b}$. These compounds are present in the mixture at relevant amounts of 40%, 15%, 13% and 5%. Thus, 73% of the mixture comprises the isotope at $Y^{9b}$ that is present in the compound. The compound plus lighter isotopologues 2, 3 and 6 comprise the isotope deuterium at position $Y^{9c}$. These compounds are present in the mixture at relevant amounts of 40%, 14%, 13% and 4%. Thus, 71% of the mixture comprises the isotope at $Y^{9c}$ that is present in the compound. Accordingly, this mixture comprises a compound and its lighter isotopologues in relative proportions such that 71% of the compounds in said mixture comprise an isotope at each position containing a stable heavy atom isotope in the full isotopic compound.

The invention also provides compositions comprising an effective amount of a compound of Formula II, or a prodrug, or prodrug salt thereof, or a solvate, hydrate, or polymorph of the foregoing; and an acceptable carrier. Preferably, a composition of this invention is formulated for pharmaceutical use ("a pharmaceutical composition"), wherein the carrier is a pharmaceutically acceptable carrier. The carrier(s) must be "acceptable" in the sense of being compatible with the other ingredients of the formulation and, in the case of a pharmaceutically acceptable carrier, not deleterious to the recipient thereof in amounts typically used in medicaments.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions of the invention include those suitable for oral, rectal, nasal, topical (including buccal and sublingual), vaginal or parenteral (including subcutaneous, intramuscular, intravenous and intradermal) administration. See Doherty P C Jr et. al. U.S. Pat. No. 6,548,490 assigned to Vivus, Inc.; Place V A, U.S. Pat. No. 6,469,016 assigned to Vivus, Inc. In certain embodiments, the compound of the formulae herein is administered transdermally (e.g., using a transdermal patch or iontophoretic techniques). Other formulations may conveniently be presented in unit dosage form, e.g., tablets and sustained release capsules, and in liposomes, and may be prepared by any methods well known in the art of pharmacy. See, for example, Remington's Pharmaceutical Sciences, Mack Publishing Company, Philadelphia, Pa. (17th ed. 1985).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers or both, and then if necessary shaping the product.

In certain preferred embodiments, the compound is administered orally. Compositions of the present invention suitable for oral administration may be presented as discrete units such as capsules, sachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion, or packed in liposomes and as a bolus, etc. Soft gelatin capsules can be useful for containing such suspensions, which may beneficially increase the rate of compound absorption. For instance, see Anderson N R and Gullapalli R P, U.S. Pat. No. 6,841,167 assigned to Lilly Icos.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface-active or dispersing agent. Molded tablets may be made by molding in a suitable machine a mixture of the powdered compound moistened with an inert liquid diluent. The tablets optionally may be coated or scored and may be formulated so as to provide slow or controlled release of the active ingredient therein. Methods of formulating such slow or controlled release compositions of pharmaceutically active ingredients, such as those herein and other compounds known in the art, are known in the art and described in several issued US patents, some of which include, but are not limited to, U.S. Pat. Nos. 4,369,172; and 4,842,866, and references cited therein. Coatings can be used for delivery of compounds to the intestine (see, e.g., U.S. Pat. Nos. 6,638,534, 5,217,720, and 6,569,457, 6,461,631, 6,528,080, 6,800,663, and references cited therein). Such coatings are of particular value in the delivery of a compound of Formula II, and more specifically for delivery of Compound 2.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added. Surfactants such as sodium lauryl sulfate may be useful to enhance dissolution and absorption.

Compositions suitable for topical administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant such as Ph. Helv or a similar alcohol.

The pharmaceutical compositions of this invention may be administered in the form of suppositories for rectal or vaginal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches and iontophoretic administration are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. Such administration is known to be effective with erectile dysfunction drugs: Rabinowitz J D and Zaffaroni A C, U.S. Pat. No. 6,803,031, assigned to Alexza Molecular Delivery Corporation.

Application of the subject therapeutics may be local, so as to be administered at the site of interest. Various techniques can be used for providing the subject compositions at the site of interest, such as injection, use of catheters, trocars, projectiles, pluronic gel, stents, sustained drug release polymers or other device which provides for internal access.

Thus, according to another embodiment, the compounds of this invention may be incorporated into compositions for coating an implantable medical device, such as prostheses, artificial valves, vascular grafts, stents, or catheters. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the invention provides a method of coating an implantable medical device comprising the step of contacting said device with the coating composition described above. It will be obvious to those skilled in the art that the coating of the device will occur prior to implantation into a mammal.

According to another embodiment, the invention provides a method of impregnating an implantable drug release device comprising the step of contacting said drug release device with a compound or composition of this invention. Implantable drug release devices include, but are not limited to, biodegradable polymer capsules or bullets, non-degradable, diffusible polymer capsules and biodegradable polymer wafers. Implantable mechanical devices are also known; see for instance Gerber M T, US Patent Applications 20050010259, 20050033372, 20050070969, assigned to Medtronic Inc.

According to another embodiment, the invention provides an implantable medical device coated with a compound or a composition comprising a compound of this invention, such that said compound is therapeutically active.

According to another embodiment, the invention provides an implantable drug release device impregnated with or containing a compound or a composition comprising a compound of this invention, such that said compound is released from said device and is therapeutically active.

Where an organ or tissue is accessible because of removal from the patient, such organ or tissue may be bathed in a medium containing a composition of this invention, a composition of this invention may be painted onto the organ, or a composition of this invention may be applied in any other convenient way.

The present invention further provides pharmaceutical compositions comprising an effective amount of one or more compound of the invention in combination with an effective amount of a second therapeutic agent useful for treating or preventing a condition selected from stable angina, unstable angina, variant angina, hypertension, pulmonary hypertension, chronic obstructive pulmonary disease, acute respiratory distress syndrome, malignant hypertension, pheochromocytoma, congestive heart failure, acute renal failure, chronic renal failure, atherosclerosis, a condition of reduced blood vessel patency, a peripheral vascular disease, a vascular disorder, thrombocythemia, an inflammatory disease, myocardial infarction, stroke, bronchitis, chronic asthma, allergic asthma, allergic rhinitis, glaucoma, peptic ulcer, a gut motility disorder, postpercutaneous transluminal coronary or carotid angioplasty, post-bypass surgery graft stenosis, osteoporosis, preterm labor, benign prostatic hypertrophy, or irritable bowel syndrome, in a human or nonhuman animal body; treatment of a sexual deficiency state in a human, including the state of female sexual dysfunction, including recurrent conditions, and treatment of patients who have a co-existing condition of epilepsy, craniopharyngioma, hypogonadism or who has had a hysterectomyoophorectomy, hysterectomy or oophorectomy; as well as hyperglycemia, hyperinsulinaemia, hyperlipidaemia, hypertriglyceridemia, diabetes, insulin resistance, impaired glucose metabolism, conditions of impaired glucose tolerance (IGT), conditions of impaired fasting plasma glucose, obesity, diabetic retinopathy, diabetic nephropathy, glomerulosclerosis, diabetic neuropathy, syndrome X, coronary heart disease, angina pectoris, vascular restenosis, endothelial dysfunction, depression, epilepsy, faintness attacks, hypokinesia, cranial disorders, neurodegenerative disorders, depression, anxiety, panic, pain, irritable bowel syndrome, sleep disorders, osteoarthritis, rheumatoid arthritis, neuropathological disorders, visceral pain, functional bowel disorders, inflammatory bowel diseases, pain associated with dysmenorrhea, pelvic pain, cystitis, pancreatitis, cyclical oedema, Menires disease, hyperaldosteroneism (primary and secondary), hypercalciuria and lower urinary tract symptoms, other than urinary incontinence, associated with overactive bladder and/or benign prostatic hyperplasia; or of inducing mating in a non-human mammal.

Such second therapeutic agents useful in combination with the compounds of this invention include, but are not limited to: a vasodilator, prostaglandin E1, prostacyclin, an α-adrenergic blocker, a mixed α,β-blocker, an $α_2$-adrenergic blocker, an ACE inhibitor, an NEP inhibitor, a centrally acting dopaminergic agent, a vasoactive intestinal peptide, a calcium channel blocker, a thiazide diuretic, (5R)-(methylamino)-5,6-dihydro-4H-imidazo[4,5,1-ij]quinolin-2(1H)-one, (5R)-(methylamino)-5,6-dihydro-4H-imidazo[4,5,1-ij]quinoline-2(1H)-thione and pharmaceutically acceptable salts thereof; a 5-HT$_2$ receptor ligand, in particular, 5-HT$_{2a}$ and 5-HT$_{2c}$ receptor ligands; an acetylcholine esterase antagonist; a vasopressin receptor family antagonist, or a pharmaceutically acceptable derivative thereof; 1-deprenyl or propargylamine compounds; human melanocortin-4 receptor (MC-4R) agonists; gamma-butyrobetaine; an alpha-2-delta ligand; an angiotensin II receptor antagonist; a prostaglandin $E_2$ receptor subtype $EP_1$ antagonist; an endothelin antagonist; an antidiabetic agent, an HMG-Co-a reductase inhibitor, a serotonin reuptake inhibitor (SSRI), or a pharmaceutically acceptable salt thereof; and combinations of the foregoing.

Examples of vasodilators include, but are not limited to, nitroglycerin, isosorbide dinitrate, pentaerythrityl tetranitrate, isosorbide-5-mononitrate, propatyl nitrate, trolnitrate, nicroandil, mannitol hexanitrate, inositol hexanitrate, N-[3-nitratopivaloyl]-6-cysteine ethyl ester, isoamyl nitrite, S-nitroso-N-acetyl-D,L-penicillamine, 1,2,5-oxadiazole-2-oxide, furazan-N-oxide, molsidomine, mesocarb, an iron nitrosyl compound, sodium nitroprusside, nitric oxide, and mixtures thereof.

Examples of a-adrenergic blockers include, but are not limited to, phentolamine and prazocin.

Examples of mixed $\alpha,\beta$-blockers include, but are not limited to, carvedilol.

Examples of $\alpha_2$-adrenergic blockers include, but are not limited to, yohimbine.

Examples of ACE inhibitors include, but are not limited to, quinapril, enalapril, captopril, spirapril, fosinopril, moexipril, enalaprilat, ramipril, perindopril, indolapril, lisinopril, alacepril, trandolapril, benazapril, libenzapril, delapril, cilazapril and combinations thereof.

Examples of NEP inhibitors include, but are not limited to, those disclosed by Hepworth D, US Patent Application 20040180941, Pfizer Applicant and Dack K N, US Patent Application 20040138274, Warner-Lambert Applicant.

Examples of centrally acting dopaminergic agents include, but are not limited to, apomorphine.

Examples of calcium channel blockers include, but are not limited to, amlodipine, diltiazem, felodipine, isradipine, nicardipine, nifedipine, and verapamil.

Examples of thiazides include, but are not limited to, hydrochlorothiazide, flumethiazide, hydroflumethiazide, bendroflumethiazide, methylchlothiazide, trichlormethiazide, polythiazide or benzthiazide.

Examples of $5-HT_{2a}$ and $5-HT_{2c}$ receptor ligands include, but are not limited to, those disclosed by Chiang P et. al. in US Patent applications 20050054656, 20050020604, and 20050032809, Pfizer Applicant.

Examples of acetylcholine esterase antagonists include, but are not limited to, donepezil, galanthamine, rivastigme, tacrine, physostigime, neostigmine, edrophonium, pyridostigmine, demecarium, pyridostigmine, phospholine, metrifonate, zanapezil, and ambenonium.

Examples of vasopressin receptor family antagonists include, but are not limited to, relcovaptan, atosiban, conivaptan, OPC21268, or 8-chloro-5-methyl-1-(3,4,5,6-tetrahydro-2H-[1,2']bipyridinyl-4-yl)-5,6-dihydro-4H-2,3,5,10b-tetraazo-benzo[e]azulene, or a pharmaceutically acceptable salt or solvate thereof; and those disclosed by Wayman C P and Russell R J, United States Patent Application 20050014848, Pfizer Applicant.

Examples of propargylamine compounds include, but are not limited to, those disclosed by Yu P H et. al., U.S. Pat. No. 5,508,311 and in references cited therein.

Examples of MC-4R agonists include, but are not limited to, those disclosed by Merck, Applicant in US Patent Applications 20030225060, 20040097546, 20040204398, and 20040266821.

Examples of alpha-2-delta ligands include, but are not limited to, gabapentin and pregabalin.

Examples of angiotensin II receptor antagonists include, but are not limited to, candesartan, eprosartan, irbesartan, losartan, olmesartan, olmesartan medoxomil, saralasin, telmisartan and valsartan and pharmaceutically acceptable salts thereof.

Examples of prostaglandin $E_2$ receptor subtype $EP_1$ antagonists include, but are not limited to, 4-[2-[N-isopropyl-N-(5-methyl-2-furylsulfonyl)amino]-5trifluoromethylphenoxymethyl]benzoic acid; 4-[2-[N-isopropyl-N-(5-methyl-2-furylsulfonyl)-amino]-4,5dimethylphenoxymethyl]benzoic acid; 3-methyl-4-[2-[N-isobutyl-N-(5-methyl-2-furylsulfonyl)amino]-4,5dimethylphenoxymethyl]benzoic acid; 4-[6-[N-isobutyl-N-(5-methyl-2-furylsulfonyl)amino]indan-5yloxymethyl]cinnamic acid; 3-methyl-4-[6-[N-isobutyl-N-(4-methyl-2-thiazolylsulfonyl)amino]indan-5yloxymethyl] cinnamic acid; 4-[4,5-dimethyl-2-[N-methyl-N-(5-methyl-2-furylsulfonyl)-N-propylamino]phenoxymethyl]benzoic acid; 4-[6-[N-isobutyl-N-(4-methyl-2-thiazolylsulfonyl) amino]indan-5yloxymethyl]benzoic acid; non-toxic salts thereof, or esters thereof.

Examples of endothelin antagonists include, but are not limited to, non-peptidal endothelin antagonists such as bosentan, ETA/ETB receptor antagonist such as PD145065, and endothelin converting enzyme such as phosphoramidon.

Examples of antidiabetic agents include, but are not limited to, insulin secretion enhancers, insulin sensitivity enhancers, insulin signaling pathway modulators, such as inhibitors of protein tyrosine phosphatases (PTPases), antidiabetic non-small molecule mimetic compounds and inhibitors of glutamine-fructose-6-phosphate amidotransferase (GFAT); compounds influencing a dysregulated hepatic glucose production, such as inhibitors of glucose-6-phosphatase (G6Pase), inhibitors of fructose-1,6-bisphosphatase (F-1,6-BPase), inhibitors of glycogen phosphorylase (GP), glucagon receptor antagonists and inhibitors of phosphoenolpyruvate carboxykinase (PEPCK); pyruvate dehydrogenase kinase (PDHK) inhibitors; inhibitors of gastric emptying; insulin; inhibitors of GSK-3; retinoid X receptor (RXR) agonists; agonists of β-3 AP; agonists of uncoupling proteins (UCPs); non-glitazone type PPARγ-agonists; dual PPARγ/PPARα agonists; antidiabetic vanadium containing compounds; incretin hormones, such as glucagon-like peptide-1 (GLP-1) and GLP-1 agonists; β-cell imidazoline receptor antagonists; miglitol; and $\alpha_2$-adrenergic antagonists.

Examples of HMG-Co-A reductase inhibitors include, but are not limited to, atorvastatin, cerivastatin, fluvastatin, pitavastatin, lovastatin, pravastatin, rosuvastatin, simvastatin, mevastatin, and the pharmaceutically acceptable salts, esters, lactones and isomeric forms thereof.

Examples of serotonin uptake inhibitors include, but are not limited to, femoxetine, fluoxetine, fluvoxamine, indalpine, indeloxazine, milnacipran, paroxetine, sertraline, sibutramine, zimeldine, citalopram, escitalopram, fenfluramine, venlafaxine, duloxetine and those disclosed by Marek G J et. al., United States Patent Application 20050014848, Pfizer Applicant.

In another embodiment, the invention provides separate dosage forms of a compound of this invention and a second therapeutic agent that are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

In the pharmaceutical compositions of the invention, the compound of the present invention is present in an effective amount. As used herein, the term "effective amount" refers to an amount which, when administered in a proper dosing regimen, is sufficient to reduce or ameliorate the severity, duration or progression, or enhance function compromised by a disorder associated with high PDE5 activity or low intracellular concentrations of cGMP, for instance in arterial walls or in the corpus cavernosal smooth muscle; to prevent the advancement of a disorder associated with low vascular or smooth muscle intracellular concentrations of cGMP, cause the regression of a disorder associated with low vascular or smooth muscle intracellular concentrations of cGMP, or enhance or improve the prophylactic or therapeutic effect(s) of another therapy.

In certain preferred embodiments, treatment according to the invention provides a reduction in or prevention of at least one symptom or manifestation of a disorder that has been linked to PDE5 activity, as determined in vivo or in vitro inhibition of at least about 10%, more preferably 20%, 30%, 40%, 50%, 60%, 70%, 80%, 90%, 95%, 98% or 99% of such activity. With respect to inhibition of PDE5 activity, the term "effective amount" means an amount that results in a detectable reduction in the ability of PDE5 to convert cAMP or cGMP or their $^{32}$P-labeled isotopologues to, respectively, 5'-AMP or 5'-GMP or their $^{32}$P-labeled isotopologues; or increase in the amount or concentration of intracellular cGMP, particularly in arterial and corpus cavemosal smooth muscle tissue, in a patient or in a biological sample; or the correction of or relief from a behavior, deficit, symptom, syndrome or disease, or enhancement of otherwise compromised function that has been linked to low intracellular cGMP levels, alone or in combination with another agent or agents; or the induction of a behavior, activity or response that has been linked to normalized or increased intracellular cGMP levels.

The interrelationship of dosages for animals and humans (based on milligrams per meter squared of body surface) is described in Freireich et al., (1966) Cancer Chemother Rep 50: 219. Body surface area may be approximately determined from height and weight of the patient. See, e.g., Scientific Tables, Geigy Pharmaceuticals, Ardley, N.Y., 1970, 537. An effective amount of a compound of this invention can range from about 0.001 mg/kg to about 500 mg/kg, more preferably 0.01 mg/kg to about 50 mg/kg, yet more preferably 0.025 mg/kg to about 1.5 mg/kg. Effective doses will also vary, as recognized by those skilled in the art, depending on the diseases treated, the severity of the disease, the route of administration, the sex, age and general health condition of the patient, excipient usage, the possibility of co-usage with other therapeutic treatments such as use of other agents and the judgment of the treating physician.

For pharmaceutical compositions that comprise a second therapeutic agent, an effective amount of the second therapeutic agent is between about 20% and 100% of the dosage normally utilized in a monotherapy regime using just that agent. Preferably, an effective amount is between about 70% and 100% of the normal monotherapeutic dose. The normal monotherapeutic dosages of the second therapeutic agents useful in this invention are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are entirely incorporated herein by reference.

It is expected that some of the second therapeutic agents listed above will act synergistically with the compounds of this invention. When this occurs, its will allow the effective dosage of the second therapeutic agent and/or the compound of this invention to be reduced from that required in a monotherapy. This has the advantage of minimizing toxic side effects of either the second therapeutic agent of a compound of this invention, synergistic improvements in efficacy, improved ease of administration or use and/or reduced overall expense of compound preparation or formulation.

Methods of Treatment

In one embodiment, the present invention provides a method of inhibiting PDE5 or increasing intracellular cGMP levels, particularly in arterial and corpus cavernosal smooth muscle, in a subject comprising the step of administering to said subject an effective amount of a compound of Formula II, preferably combined in a composition with a pharmaceutically acceptable carrier.

Preferably the method is employed to treat a subject suffering from or susceptible to one or more disease or disorder selected from erectile dysfunction, stable, unstable and variant angina, hypertension, pulmonary hypertension, chronic obstructive pulmonary disease, acute respiratory distress syndrome, malignant hypertension, pheochromocytoma, congestive heart failure, acute renal failure, chronic renal failure, atherosclerosis, conditions of reduced blood vessel patency, peripheral vascular diseases, vascular disorders, thrombocythemia, inflammatory diseases, myocardial infarction, stroke, bronchitis, chronic asthma, allergic asthma, allergic rhinitis, glaucoma, peptic ulcer, gut motility disorders, post-percutaneous transluminal coronary or carotid angioplasty, post-bypass surgery graft stenosis, osteoporosis, preterm labor, benign prostatic hypertrophy, and irritable bowel syndrome, in humans and in animals; erectile dysfunction in male humans and animals; and female arousal disorder in females. The method can also be employed to treat a subject suffering from or susceptible to one or more disease or disorder selected from low sperm count in males preventing successful fertilization of an ovum; reducing insulin resistance; preventing ischemia/reperfusion injury; preventing or treating a condition involving fibrosis; and for alleviating pain or spasticity in a patient suffering from spinal cord injury. Other embodiments include any of the methods herein wherein the subject is identified as in need of the indicated treatment.

Preferably, the method is used to treat a sexual disorder or a cardiovascular disorder, More preferably, the sexual disorder is selected from erectile dysfunction or female arousal disorder. Most preferably, the condition to be treated is erectile dysfunction.

Another aspect of the invention is a compound of Formula II for use in increasing intracellular cGMP levels or inhibiting PDE5. Preferably that use is in the treatment or prevention in a subject of a disease, disorder or symptom set forth above.

Another aspect of the invention is use of a compound of Formula II in the manufacture of a medicament for increasing intracellular cGMP levels or inhibiting PDE5. Preferably, the medicament is used for treatment or prevention in a subject of a disease, disorder or symptom set forth above.

In another embodiment, the method of treating one of the diseases, disorders or symptoms set forth above further comprises the step of administering to said patient a second therapeutic agent which alone or in combination with Compound 1 is effective to sexually deficient states in humans with epilepsy, craniopharyngioma, hypogonadism, or who have had a hysterectomyoophorectomy, hysterectomy or oophorectomy; or to induce mating in non-human animals.

In yet another embodiment, the method of treatment comprises the further step of administering to said patient a second therapeutic agent which alone or in combination with Compound 1 is effective to treat one or more of hyperglycemia, hyperinsulinaemia, hyperlipidaemia, hypertriglyceridemia, diabetes, insulin resistance, impaired glucose metabolism, conditions of impaired glucose tolerance (IGT), conditions of impaired fasting plasma glucose, obesity, diabetic retinopathy, diabetic nephropathy, glomerulosclerosis, diabetic neuropathy, syndrome X, coronary heart disease, angina pectoris, vascular restenosis, endothelial dysfunction, depression, epilepsy, faintness attacks, hypokinesia, cranial disorders, neurodegenerative disorders, depression, anxiety, panic, pain, irritable bowel syndrome, sleep disorders, osteoarthritis, rheumatoid arthritis, neuropathological disorders, visceral pain, functional bowel disorders, inflammatory bowel diseases, pain associated with dysmenorrhea, pelvic pain, cystitis, pancreatitis, cyclical oedema, Menires disease, hyperaldosteroneism (primary and secondary), hypercalciuria and lower urinary tract symptoms, other than urinary incontinence, associated with overactive bladder and/or benign prostatic hyperplasia.

The second therapeutic agent may be administered together with a compound of Formula II as part of a single dosage form or as multiple dosage forms. Alternatively, the second therapeutic agent may be administered prior to, consecutively with, or following the administration of a compound of this invention. In such combination therapy treatment, both the compounds of this invention and the second therapeutic agent(s) are administered by conventional methods. The administering of the second therapeutic agent may occur before, concurrently with, and/or after the administering of the compound of this invention. When the administration of the second therapeutic agent occurs concurrently with a compound of this invention, the two (or more) agents may be administered in a single dosage form (such as a composition of this invention comprising a compound of the invention and a second therapeutic agent as described above), or in separate dosage forms. The administration of a composition of this invention comprising both a compound of the invention and an additional therapeutic agent to a subject does not preclude the separate administration of said therapeutic agent, any other therapeutic agent or any compound of this invention to said subject at another time during a course of treatment.

Effective amounts of a second therapeutic agent useful in the methods of this invention are well known to those skilled in the art and guidance for dosing may be found in patents referenced herein. However, it is well within the skilled artisan's purview to determine the other therapeutic agent's optimal effective-amount range. In one embodiment of the invention where a second therapeutic agent is administered to an animal, the effective amount of the compound of this invention is less than its effective amount would be where the second therapeutic agent is not administered. In another embodiment, the effective amount of the second therapeutic agent is less than its effective amount would be where the compound of this invention is not administered. In this way, undesired side effects associated with high doses of either agent may be minimized. Other potential advantages (including without limitation improved dosing regimens and/or reduced drug cost) will be apparent to those of skill in the art.

Second therapeutic agents useful in the method of treatment of this invention are the same as those described above as part of combination compositions.

According to another aspect, the invention provides a compound of Formula II and one or more of the above-described second therapeutic agents, either in a single composition or as separate dosage forms for use in the treatment or prevention in a subject of a disease, disorder or symptom set forth above.

In yet another aspect, the invention provides the use of a compound of Formula II and one or more of the above-described second therapeutic agents in the manufacture of a medicament, either as a single composition or as separate dosage forms, for treatment or prevention in a subject of a disease, disorder or symptom set forth above.

The compounds of this invention may be assayed in vitro by known methods. For instance, human PDE5 inhibition assays, and the related phosphodiesterases PDE3, PDE4, and PDE6, are commercially available from MDS Pharma Services. Cerep (Paris, France) provides commercial assays for PDE1, PDE2, PDE3, PDE4, PDE5 and PDE6. Methodology for such assays is also well known; see for instance Komas N et. al., Br. J. Pharmacol 1991 104: 495; Wells J N, Biochim. Biophys. Acta 1975 19: 430; and Rotella D P et. al., J. Med. Chem. 2000 43: 1257. Increases in intracellular levels of cGMP in appropriate tissue is also readily determined; see for instance Daugan A C-M and Gellibert F, U.S. Pat. No. 6,143,746 to ICOS. Thus, both enzymatic activity and specificity for compounds of this invention, as well as cellular efficacy, are readily determined.

Animal models measuring antihypertensive activity are also available and provide predictive in vivo measurement of PDE5 inhibitors' ability to effect vasodilatation by increases in arterial smooth muscle cGMP levels as well as the potency and length of action of the inhibitors. See e.g. Daugan A C-M and Gellibert F, U.S. Pat. No. 6,143,746 to ICOS; Daugan A et. al. J. Med. Chem. 2003 46: 4533. Each of the compounds of this invention may be tested by such means. The compounds of this invention may also be tested by in vitro assays, to quantify their activity, resistance to liver metabolism by cellular or tissue exposure, or by isolated metabolic enzymes such as CYP3A4, or by in vivo pharmacokinetic measurement (available commercially, e.g. from SRI Biosciences, Menlo Park, Calif.; Covance, Princeton N.J.; Charles River Laboratories, Wilmington, Mass.; and Cerep, Seattle Wash.; among others) and compared to Compound 1.

Diagnostic Methods and Kits

According to another embodiment, the invention provides a method of determining the concentration of Compound 1 in a biological sample, said method comprising the steps of:

a) adding a known concentration of a second compound to said biological sample, said second compound having the formula:

Formula II:

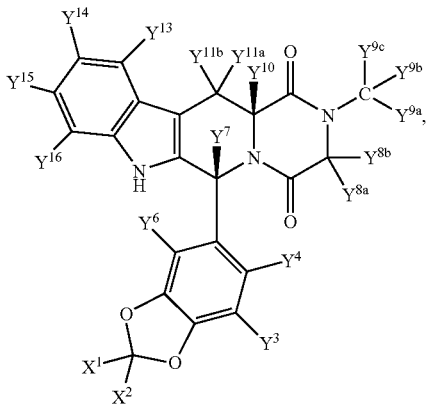

wherein:

$X^1$ and $X^2$ are simultaneously fluoro; or $X^1$ is deuterium and $X^2$ is selected from hydrogen or deuterium;

each Y is independently selected from deuterium or hydrogen;

the hydrogen attached to the indole nitrogen is optionally replaced by deuterium; each carbon is independently optionally replaced by $^{13}C$; and wherein at least hydrogen is replaced by deuterium or at least one carbon is replaced by 13C;

b) subjecting said biological sample to a measuring device that distinguishes Compound 1 from said second compound;

c) calibrating said measuring device to correlate the detected quantity of Compound 1 with the known concentration of said second compound added to said biological sample; and d) determining the concentration of said compound in said biological sample by comparing the detected quantity of Compound 1 with the detected quantity and known concentration of said second compound.

In one preferred embodiment, said second compound has the formula:

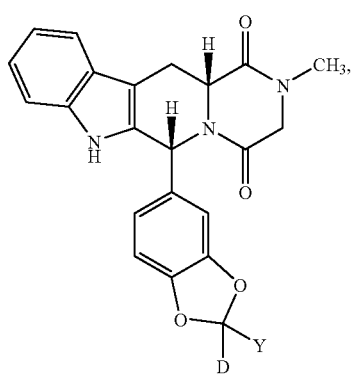

(IV)

wherein:

Y is hydrogen or deuterium and;

each hydrogen atom is optionally substituted by deuterium and each carbon atom is optionally substituted by $^{13}C$.

Measuring devices that can distinguish Compound 1 from said second compound include any measuring device that can distinguish between two compounds that are of identical structure except that one contains one or more heavy atom isotope versus the other. Preferably, such a measuring device is a mass spectrometer.

In a preferred embodiment, at least three combined hydrogen atoms and carbons are, respectively, replaced by deuterium and $^{13}C$ in said second compound; i.e. (total number of D)+(number of $^{13}C$)≧3.

In another preferred embodiment, the method comprises the additional step of organically extracting both Compound 1 and said second compound from said biological sample prior to step b).

Compound 1 and the second compound will have similar solubility, extraction, and chromatographic properties, but significantly different molecular mass. Thus, the second compound is useful as an internal standard in a method that comprises the step of organic extraction to measure the efficiency of that extraction and to ensure an accurate determination of the true concentration of Compound 1 (see Tuchman M and McCann M T, Clin. Chem. 1999 45: 571; Leis H J et. al., J. Mass Spectrom. 2001 36: 923; Taylor R L et. al. Clin. Chem. 2002 48: 1511).

The compounds of the present invention (the second compound) are particularly useful in this method since they are not radioactive and therefore do not pose a hazard to personnel handling the compounds. Thus, these methods do not require precautions beyond those normally applied in clinical sample analysis.

Furthermore, stably labeled isotopes have long been used to assist in research into the enzymatic mechanism of cytochrome P450 enzymes (Korzekwa K R et. al., Drug Metab. Rev. 1995 27: 45 and references therein; Kraus, J A and Guengerich, F P, J. Biol. Chem. 2005 280: 19496; Mitchell K H et. al., Proc. Natl. Acad. Sci. USA 2003 109: 3784).

In another embodiment, the invention provides a diagnostic kit comprising:

a) a compound having the compound having the formula: II:

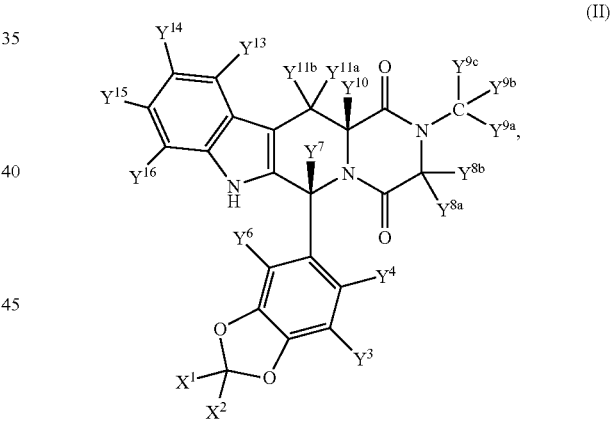

(II)

wherein:

$X^1$ and $X^2$ are simultaneously fluoro; or $X^1$ is deuterium and $X^2$ is selected from hydrogen or deuterium;

each Y is independently selected from deuterium or hydrogen;

the hydrogen attached to the indole nitrogen is optionally replaced by deuterium;

each carbon is independently optionally replaced by $^{13}C$; and at least hydrogen is replaced by deuterium or at least one carbon is replaced by $^{13}C$; and b) instructions for using said compound to determine the concentration of a test compound in a biological sample.

In a preferred embodiment, said compound has the formula:

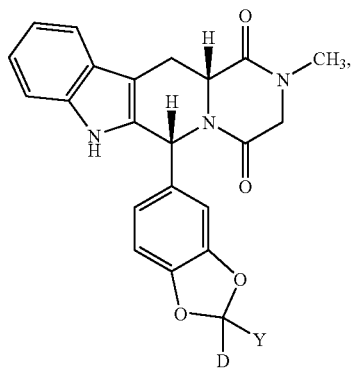

wherein:

Y is hydrogen or deuterium and;

each hydrogen atom is optionally substituted by deuterium and each carbon atom is optionally substituted by 13C.

In another embodiment, the invention provides a method of evaluating the metabolic stability of a compound of formula II, comprising the steps of contacting the compound of formula II with a metabolizing enzyme source for a period of time; and comparing the amount of said compound to the metabolic products of said compound after said period of time.

In one preferred embodiment, the method comprises an additional step of comparing the amount of said compound to said metabolic products of said compound at an interval during said period of time. This method allows the determination of a rate of metabolism of said compound.

In another preferred embodiment, the method comprises the additional steps of contacting a compound of formula II with said metabolizing enzyme source; comparing the amount of said compound of formula II to the metabolic products of said compound of formula II after said period of time determining a rate of metabolism of said compound of formula I; and comparing the metabolic stability of Compound 1 to said compound of formula II. This method is useful in determining whether and at which sites on a compound of formula II additional deuterium or $^{13}C$ substitution would cause increases in metabolic stability. It is also useful in comparing the metabolic stability of a compound of formula II with the metabolic stability of Compound 1.

A metabolizing enzyme source may be a purified, isolated or partially purified metabolic protein, such as a cytochrome P450; a biological fraction, such as a liver microsome fraction; or a piece of a metabolizing organ, such as a liver slice.

The determination of the amount of compound and its metabolic products is well known in the art. It is typically achieved by removing an aliquot from the reaction mixture and subjecting it to an analysis capable of distinguishing between the compound and its metabolites, such as reversed-phase HPLC with UV absorption or mass spectroscopic detection. Concentrations of both the metabolizing enzyme and the compound may be varied to determine kinetic parameters, for instance, by using appropriate nonlinear regression software such as is known in the art. By comparing the kinetic parameters of both a compound of formula II and Compound 1 an apparent steady-state deuterium isotope effect ($^D(V/K)$) can be determined as the ratio of products formed in the hydrogen versus deuterium reactions.

The determination of a rate of metabolism of a compound of formula I may be achieved in a reaction separate from the reaction for determining the metabolism rate of Compound 1. Alternatively, Compound 1 may be admixed with a compound of formula I in a competition experiment to determine rates of disappearance of the two compounds, making use of analytical instrumentation capable of differentiating between the two compounds based on their mass differences.

In yet another embodiment, pre-steady state kinetics, such as $V_0$, may be determined by means known in the art, for instance, using quench-flow apparatus, by monitoring the quenched reactions at varying times after mixing the compound or isotopologue with the metabolizing enzyme source.

In a related embodiment, the invention provides a kit comprising, in separate vessels: a) Compound 1; and b) a metabolizing enzyme source. The kit is useful for comparing the metabolic stability of a compound of formula II with Compound 1, as well as evaluating the effect of deuterium and $^{13}C$ replacement at various positions on a compound of formula II. In a preferred embodiment, the kit further comprises instructions for using Compound 1 and said metabolizing enzyme source to evaluate the metabolic stability of a compound of formula II.

In order that the invention might be more fully understood, the following examples are set forth. They are not intended to limit the scope of the invention and further examples will be evident to those of ordinary skill in the art. In each example set forth herein, carbon shall be $^{12}C$, and hydrogen shall by $^1H$, each incorporated at its natural abundance, unless otherwise specified.

Example 1

2,2-Difluorobenzo[d][1,3]dioxole-5-carbaldehyde. A solution of 127 mmol of 5-bromo-2,2-difluorobenzo[d][1,3]dioxole in 200 mL of THF is cooled under argon in a $CO_2$/acetone bath and treated with 1.05 equivalents of n-BuLi in THF. The mixture is stirred for about 10 min in the cold, then treated with 1.2 equivalents of DMF. The mixture is stirred for 30 min in the cold, then the cold bath is removed and the reaction is stirred for 1.5 h at ambient temperature and then quenched with 150 mL of saturated ammonium chloride solution. The organic layer is separated and the aqueous layer is washed 2× with ether. The combined organics are washed with brine, dried over $MgSO_4$ and concentrated in vacuo. Silica gel chromatography (EtOAc/hexanes eluant) yields the title compound.

Example 2

5-Bromo-6-deutero-2,2-difluorobenzo[d][1,3]dioxole. A solution of 24 mmol of 5,6-dibromo-2,2-difluorobenzo[d][1,3]dioxole (Chemos GmbH, Regenstauf, Germany) in 40 mL of THF is cooled under argon in a $CO_2$/acetone bath and treated with 0.98 equivalents of n-BuLi in THF. The mixture is stirred for about 10 min in the cold, then treated with 1 mL of $D_2O$. The mixture is stirred for 15 min in the cold, then the cold bath is removed and stirring is continued for 1.5 h, then quenched with 40 mL of saturated ammonium chloride solution. The organic layer is then separated and the aqueous layer is washed 2× with ether. The combined organics are washed with brine, dried over $MgSO_4$ and concentrated in vacuo. Silica gel chromatography (ether/hexanes eluant) yields the title compound.

Example 3

6-Deutero-2,2-difluorobenzo[d][1,3]dioxole-5-carbaldehyde. A 13.2 mmol portion of the product of Example 2 is formylated using the general procedure described in example 1 yielding, after silica gel chromatography with EtOAc/hexanes eluant, the title product.

Example 4

2,2-Difluorobenzo[d][1,3]dioxole-5-deuterocarbaldehyde. A 32.2 mmol sample of 5-bromo-2,2-difluorobenzo[d][1,3]dioxole is formylated using the general procedure described in example 1 except using N,N-dimethylformamide-1-d as the formylating reagent to yield, after silica gel chromatography with EtOAc/hexanes eluant, the title product.

Example 5

(1R,3R)-Methyl 1-(2,2-difluorobenzo[d]-dioxol-5-yl)-2,3,4,9-tetrahydro-1H-pyrido[3,4,-b]indole-3-carboxylate (Formula IV, wherein E is methyl and each Y group is hydrogen). A solution of 37.4 mmol of D-tryptophan methyl ester and 41.1 mmol of the product of Example 1 in 220 mL of methylene chloride is cooled under argon in a −5° C. bath and treated with 5.4 mL of trifluoroacetic acid. The mixture is stirred for 30 min, the ice bath is removed, and stirring is continued for 17 h at room temperature. The reaction is again cooled in an ice bath and rendered slightly basic (pH~8.5-9) by portionwise addition of saturated $NaHCO_3$ solution. After stirring an additional 45 min, the reaction is washed with 1 N $NaHCO_3$ and the aqueous layer extracted twice with additional methylene chloride. The combined organic layers are washed with half-saturated brine, dried over $MgSO_4$ and concentrated, yielding the title compound. Silica gel flash chromatography ($CH_3OH/CH_2Cl_2$ eluent) yields the title product as the faster-moving product component while later fractions comprise the (1S,3R) stereoisomer.

Example 6

(1R,3R)-Methyl 2-(2-chloroacetyl)-1-(2,2-difluorobenzo[d]-dioxol-5-yl)-2,3,4,9-tetrahydro-1H-pyrido[3,4,-b]indole-3-carboxylate (Formula V, wherein E is methyl and each Y group is hydrogen). A 12.7 mmol portion of the product of example 5 in 80 mL of methylene chloride is treated with 15.2 mmol of sodium bicarbonate and cooled in an ice/water bath under an argon atmosphere. The mixture is stirred vigorously and treated dropwise with 30.7 mmol of chloroacetyl chloride. After stirring for 10 min the ice bath is removed and stirring is continued for 1.5 h at room temperature. The mixture is partitioned between 150 mL each ether and saturated $NaHCO_3$, and the organic layer is washed with water, then brine, and dried over $MgSO_4$ and concentrated in vacuo. The resulting product is used in subsequent reactions without further purification.

Example 7

(6R,12aR)-6-(2,2-Difluorobenzo[d]-1,3-dioxol-5-yl)-1,2,3,4,6,7,12,12a-octahydropyrazino[1',2':1,6]pyrido[3,4-b]indole-2-trideuteromethyl-1,4-dione (Formula III wherein $Y^{9a}$, $Y^{9b}$, and $Y^{9c}$ are deuterium and all other Y groups are hydrogen). A solution of 8.2 mmol of the product of example 6 in 30 mL of methanol is treated with 41 mmol of methylamine-$d_5$ (Isotec) as an 18% solution in methanol. The mixture is heated at 50° C. under argon for 17 h, then concentrated in vacuo. The residue is dissolved in methylene chloride and washed with water (2×) and half saturated brine, then dried over $MgSO_4$ and concentrated in vacuo. Silica gel chromatography with methylene chloride/methanol as eluant yields the title product.

Example 8

(1R,3R)-Methyl 1-(6-deutero-2,2-difluorobenzo[d]-dioxol-5-yl)-2,3,4,9-tetrahydro-1H-pyrido[3,4,-b]indole-3-carboxylate (Formula IV, wherein E is methyl, $Y^4$ is deuterium and all other Y groups are hydrogen). A sample of the product of Example 3 (6.6 mmol) is reacted with 38.5 mmol of D-tryptophan methyl ester using the general procedure described in example 5, yielding the mixed cis-trans product. Silica gel flash chromatography ($CH_3OH/CH_2Cl_2$ eluent) of the product of example 8 gives the title product as the faster-moving product component.

Example 9

(6R,12aR)-6-(6-Deutero-2,2-difluorobenzo[d]-1,3-dioxol-5-yl)-2-methyl-1,2,3,4,6,7,12,12a-octahydropyrazino[1',2':1,6]pyrido[3,4-b]indole-1,4-dione (Formula III wherein $Y^4$ is deuterium and all other Y groups are hydrogen). A portion of the product of example 8 (8.7 mmol) is reacted with methylamine (as a 33% (weight) solution in ethanol) using the general procedure described in example 6 yielding, after silica gel chromatography with methylene chloride/methanol as eluant, the title product.

Example 10

(1S,3R)-Methyl 1-(2,2-difluorobenzo[d][1,3]dioxol-5-yl)-1-deutero-2-propionyl-2,3,4,9-tetrahydro-1H-pyrido[3,4-b]indole-3-carboxylate (Formula IV, wherein E is methyl, $Y^7$ is deuterium and all other Y groups are hydrogen). An 18.7 mmol sample of the product of Example 4 is subjected to Pictet-Spengler cyclization with 20.6 mmol of D-tryptophan methyl ester and 2.7 mL of $CF_3CO_2D$ using the general procedure described in Example 5 yielding, after silica gel chromatography with methylene chloride/methanol as eluant, the title product as the faster-moving product component.

Example 11

(1R,3R)-Methyl 2-(2-chloroacetyl)-1-deutero-1-(2,2-difluorobenzo[d]-dioxol-5-yl)-2,3,4,9-tetrahydro-1H-pyrido[3,4,-b]indole-3-carboxylate (Formula V, wherein E is methyl, $Y^7$ is deuterium and all other Y groups are hydrogen). A 5.7 mmol portion of the product of Example 10 is chloracetylated according to the general procedure described in Example 6. The resulting product is used in subsequent reactions without further purification.

Example 12

(6R,12aR)-6-Deutero-6-(2,2-difluorobenzo[d]-1,3-dioxol-5-yl)2-methyl-1,2,3,4,6,7,12,12a-octahydropyrazino[1',2':1,6]pyrido[3,4-b]indole-1,4-dione (Formula III wherein $Y^7$ is deuterium and all other Y groups are hydrogen). A solution of 3.9 mmol of the product of Example 11 is reacted with methylamine using the general procedure described in Example 9 yielding, after silica gel chromatography with methylene chloride/methanol as eluant, the title product.

Example 13

(1R,3R)-Methyl 2-(2-dideuterochloroacetyl)-1-(2,2-difluorobenzo[d]-dioxol-5-yl)-2,3,4,9-tetrahydro-1H-pyrido[3,4,-b]indole-3-carboxylate (Formula V, wherein E is methyl, $Y^{8a}$ and $Y^{8b}$ are deuterium and all other Y groups are hydrogen). A solution of 6.8 mmol of chloroacetic acid-$d_3$ (C/D/N Isotopes) and 7.2 mmol of diisopropylethylamine in 18 mL of methylene chloride is cooled in an ice/methanol bath under argon and treated dropwise with 6.8mmol of pivaloyl chloride. The solution is stirred for 20 min, then treated with a solution of 4.5 mmol of the product of example 5 and 4.5 mmol of diisopropylethylamine in 2 mL of methylene chloride. The solution is stirred for 16 h at 0° C., then partitioned between 15 mL each of ether and saturated NaHCO$_3$, and the organic layer is washed brine, dried over MgSO$_4$ and concentrated in vacuo. The product is used for subsequent reactions without further purification.

Example 14

(6R,12aR)-3,3-Dideutero-6-(2,2-difluorobenzo[d]-1,3-dioxol-5-yl)-2-methyl-1,2,3,4,6,7,12,12a-octahydropyrazino[1',2':1,6]pyrido[3,4-b]indole-1,4-dione (Formula III wherein $Y^{8a}$ and $Y^{8b}$ are deuterium and all other Y groups are hydrogen). The entire product of the product of Example 13, save a ~2 mg retained portion, are reacted with methylamine using the general procedure described in Example 9 yielding, after silica gel chromatography with methylene chloride/methanol as eluant, the title product.

Example 15

(6R,12aR)-6-Deutero-6-(2,2-difluorobenzo[d]-1,3-dioxol-5-yl)-methyl-$^{13}$C-1,2,3,4,6,7,12,12a-octahydropyrazino[1',2':1,6]pyrido[3,4-b]indole-1,4dione (Formula III wherein $Y^7$ is deuterium and all other Y groups are hydrogen, and the N-methyl group is substituted with $^{13}$C). A heavy-walled pressure vial is charged with a 2.6 mmol portion of product of example 11 in 12 mL of methanol. The solution is treated with 5.2 mmol of methyl-$^{13}$C-amine hydrochloride (Isotec) and 5.2 mmol of diisopropylethylamine. The vial is sealed and heated at 50° C. for 16 h, then the reaction is concentrated in vacuo, the residue partitioned between methylene chloride and water, and the organic layer washed with half saturated brine, dried over MgSO$_4$, and concentrated in vacuo. Silica gel chromatography with methylene chloride/methanol as eluant yields the title compound.

Example 16

(1R,3R)-Methyl 2-(2-chloroacetyl-2-$^{13}$C)-1-deutero-1-(2,2-difluorobenzo[d]-dioxol-5-yl)-2,3,4,9-tetrahydro-1H-pyrido[3,4,-b]indole-3-carboxylate (Formula V, wherein E is methyl, $Y^7$ is deuterium and all other Y groups are hydrogen and the chloroacetyl methylene group is substituted with $^{13}$C). A 1.8 mmol portion of the product of Example 10 is chloroacetylated using the general procedure described in Example 13 except substituting chloroacetic acid-2-$^{13}$C (Isotec) in place of chloroacetic acid-$d_3$. Following workup, the product is used without subsequent purification.

Example 17

(6R,12aR)-6-Deutero-6-(2,2-difluorobenzo[d]-1,3-dioxol-5-yl)-methyl-1,2,3,4,6,7,12,12a-octahydropyrazino[1',2':1,6]pyrido[3,4-b]indole-1,4-dione-3-$^{13}$C (Formula III wherein $Y^7$ is deuterium and all other Y groups are hydrogen, and the unsubstituted methylene of the dioxopiperazine ring is substituted with $^{13}$C). The entire product of the product of Example 16, save a ~2 mg retained portion, are reacted with methylamine using the general procedure described in Example 9 yielding, after silica gel chromatography with methylene chloride/methanol as eluant, the title product.

Example 18

(6R,12aR)-6-(2,2-Difluorobenzo[d]-1,3-dioxol-5-yl)-1,2,3,4,6,7,12,12a-octahydropyrazino[1',2':1,6]pyrido[3,4-b]indole-2-methyl-1,4-dione (Compound 2). A solution of 31.7 mmol of the product of example 6 in 100 mL of methanol is treated with 160 mmol of methylamine as a 33% solution in ethanol. The mixture is heated at 50° C. under argon for 18 h, then concentrated in vacuo. The residue is dissolved in methylene chloride and washed with water (2×) and half saturated brine, then dried over MgSO$_4$ and concentrated in vacuo. Silica gel chromatography with methylene chloride/methanol as eluant yields the title product.

Example 19

Deuterodibromomethane. A solution of 1.1 mole of sodium deuteroxide in 140 mL of deuterium oxide is treated under argon with 116 mmol of arsenious oxide to form a solution of sodium arsenite. Bromoform (190 mmol) is treated under argon with 6.5 mL of ethanol-d (CH$_3$CH$_2$OD) and 1 mL of the sodium arsenite solution and warmed briefly (heat gun) to initiate reaction. The remainder of the sodium arsenite solution is added via dropping funnel at a rate to maintain gentle reflux. Then the mixture is heated in a 100° C. oil bath for an additional 4.5 h. The mixture is azeotropically distilled, then the distillate is separated and the aqueous layer extracted with 15 mL of pentane. The organic layers are combined, dried over CaCl$_2$, and distilled to yield the title compound.

Example 20

2-deuterobenzo[d][1,3]dioxole-5-carbaldehyde (Formula XII wherein $X^1$ is D and $X^2$ is H). A solution of 3,4-dihydroxybenzaldehyde (20 mmol) in 60 mL of dimethylformamide (DMF) is treated under argon with 60 mmol of the product of example 1 and 70 mmol of CsF. The mixture is heated in a 140° C. oil bath for 3 h with vigorous stirring. The mixture is then filtered, concentrated in vacuo, and the residue is purified by silica gel flash chromatography (ether/hexanes eluant), yielding the title product.

Example 21

2,2-dideuterobenzo[d][1,3]dioxole-5-carboxaldehyde (Formula XII wherein $X^1=X^2=D$). To a solution of 3,4-dihydroxybenzaldehyde (4.8 g, 32.1 mmol) in anhydrous DMF (120 mL) was added cesium carbonate (15.7 g, 48.2 mmol) followed by dideuterodiiodomethane (13 g, 48.2 mmol). The resulting mixture was heated at 110° C. for 2 hours, cooled to room temperature, diluted with water (300 mL), and extracted with MTBE (3×300 mL). The combined organic layers were washed with 10 wt % potassium carbonate (200 mL), brine (2×400 mL), dried over sodium sulfate, and evaporated in vacuo to give the title product as brown oil in quantitative yield.

Example 22

(1R,3R)-Methyl 1-(2-deuterobenzo[d]-dioxol-5-yl)-2,3,4,9-tetrahydro-1H-pyrido[3,4,-b]indole-3-carboxylate (Formula XIII, wherein $X^1$ is D, $X^2$ is H, and E is methyl). A solution of 12.7 mmol of D-tryptophan methyl ester and 13.9 mmol of the product of Example 21 in 80 mL of methylene chloride is cooled under argon in a −5° C. bath and treated with 1.9 mL of deuterotrifluoroacetic acid ($CF_3CO_2D$). The mixture is stirred for 30 min, the ice bath is removed, and stirring is continued for 21 h at room temperature. The reaction is again cooled in an ice bath and rendered slightly basic (pH~8.5-9) by portionwise addition of saturated $NaHCO_3$ solution. After stirring an additional 45 min, the reaction is washed with 1 N $NaHCO_3$ and the aqueous layer extracted twice with additional methylene chloride. The combined organic layers are washed with half-saturated brine, dried over $MgSO_4$ and concentrated, yielding the title compound. Silica gel flash chromatography ($CH_3OH/CH_2Cl_2$ eluent) yields the title product as the faster-moving product component while later fractions comprise the (1S,3R) stereoisomer.

Example 23

(1R,3R)-Methyl 2-(2-chloroacetyl)-1-(2-deuterobenzo[d]-dioxol-5-yl)-2,3,4,9-tetrahydro-1H-pyrido[3,4,-b]indole-3-carboxylate (Formula XIV wherein $X^1$ is D, $X^2$ is H, and E is methyl). A 4.1 mmol portion of the product of Example 22 in 30 mL of methylene chloride is treated with 5.0 mmol of sodium bicarbonate and cooled in an ice/water bath under an argon atmosphere. The mixture is stirred vigorously and treated dropwise with 9.9 mmol of chloroacetyl chloride. After stirring for 10 min the ice bath is removed and stirring is continued for 1.5 h at room temperature. The mixture is partitioned between 60 mL each ether and saturated $NaHCO_3$, and the organic layer is washed with water, then brine, and dried over $MgSO_4$ and concentrated in vacuo. Crystallization from ether/hexanes yields the title product.

Example 24

(6R,12aR)-6-(2-deuterobenzo[d]-1,3-dioxol-5-yl)-2-methyl-1,2,3,4,6,7,12,12a-octahydropyrazino[1',2':1,6]pyrido[3,4-b]indole-1,4-dione (Formula IV wherein Y=H). A solution of 1.8 mmol of the product of Example 23 in 30 mL of methanol is treated with 9 mmol of methylamine (as a 33% (weight) solution in ethanol). The mixture is heated at 50° C. under argon for 17 h, then concentrated in vacuo. The residue is dissolved in methylene chloride and washed with water (2×) and half saturated brine, then dried over $MgSO_4$ and concentrated in vacuo. Recrystallization from 2-propanol yields the title compound.

Example 25

(1R,3R)-Methyl 1-(2,2-dideuterobenzo[d]-dioxol-5-yl)-2,3,4,9-tetrahydro-1H-pyrido[3,4,-b]indole-3-carboxylate (Formula XIV, wherein $X^1$=$X^2$=D, and E is methyl). To a suspension of O-tryptophan methyl ester hydrochloride (22.9 g, 90 mmol) in anhydrous DCM (250 mL) at 0° C. was added triethylamine (12.6 mL, 90 mmol). To the solution formed above was added a solution of Example 21 (ca. 98.8 mmol) in anhydrous DCM (200 mL) followed by 4 Å molecular sieves (powder, 25 g). Then TFA (13.5 mL, 180 mmol) was added dropwise at 0° C. After addition the reaction mixture was stirred at room temperature for 5 days. After the reaction was deemed over 70% complete, it was quenched by slowly adding saturated sodium bicarbonate (300 mL). The mixture was filtered over a celite cake and washed with DCM. The aqueous layer was separated and extracted with DCM (2×300 mL). The combined organic layers were dried over sodium sulfate and evaporated in vacuo to give a crude residue that was purified on a silica gel column with 1% MeOH in DCM as eluent to give the title product (10.1 g) as a tan foam.

Example 26

(1R,3R)-Methyl 2-(2-chloroacetyl)-1-(2,2-dideuterobenzo[d]-dioxol-5-yl)-2,3,4,9-tetrahydro-1H-pyrido[3,4,-b]indole-3-carboxylate (Formula XV wherein $X^1$=$X^2$=D, Z=Cl, and E is methyl). To a solution of Example 25 (4.29, 11.9 mmol) and triethylamine (3.4 mL, 23.8 mmol) in anhydrous DCM (100 mL) at 0° C. was added dropwise chloroacetyl chloride (1.14 mL, 14.3 mmol). The reaction mixture was stirred 2 hours at 0° C. and quenched with water (100 mL). The aqueous layer was separated and extracted with DCM (2×100 mL). The combined organic layers were dried over sodium sulfate and evaporated in vacuo to give the title compound as tan foam.

Example 27

(6R,12aR)-6-(2,2-dideuterobenzo[d]-1,3-dioxol-5-yl)-2-methyl-1,2,3,4,6,7,12,12a-octahydropyrazino[1',2':1,6]pyrido[3,4-b]indole-1,4-dione (Formula II wherein $X^1$=$X^2$=D). The crude residue of Example 26 was dissolved in 2.0 M methylamine (100 mL) and stirred overnight at room temperature. The precipitate was filtered and washed with small amount of methanol to give the title compound (2.2 g) as a white fluffy solid.

Example 28

(1R,3R)-Methyl 2-(2-chloroacetyl-2-$^{13}$C)-1-(2,2-dideuterobenzo[d]-dioxol-5-yl)-2,3,4,9-tetrahydro-1H-pyrido[3,4,-b]indole-3-carboxylate. A solution of 2.3 mmol of chloroacetic acid-2-$^{13}$C (Isotec) and 2.3 mmol of diisopropylethylamine in 4 mmol of methylene chloride is cooled in an ice/methanol bath under argon and treated dropwise with 2.2 mmol of pivaloyl chloride. The solution is stirred for 20 min, then treated with a solution of 2.2 mmol of the product of Example 25 and 2.2 mmol of diisopropylethylamine in 1 mL of methylene chloride. The solution is stirred for 16 h at 0° C., then partitioned between 15 mL each of ether and saturated $NaHCO_3$, and the organic layer is washed brine, dried over $MgSO_4$ and concentrated in vacuo. Crystallization from ether/hexanes yields the title product.

Example 29

(6R,12aR)-6-(2,2-dideuterobenzo[d]-1,3-dioxol-5-yl)-2-methyl-1,2,3,4,6,7,12,12a-octahydropyrazino[1',2':1,6]pyrido[3,4-b]indole-1,4-dione-3-$^{13}$C. A solution of 0.6 mmol of the product of Example 28 is reacted with methylamine using the general procedure described in Example 24 yielding, after crystallization from 2-propanol, the title product.

Example 30

(6R,12aR)-6-(2,2-dideuterobenzo[d]-1,3-dioxol-5-yl)-1,2,3,4,6,7,12,12a-octahydropyrazino[1',2':1,6]pyrido[3,4-b]indole-2-trideuteromethyl-1,4-dione. (Formula II wherein $X^1$=$X^2$=D and $Y^{9a}$=$Y^{9b}$=$Y^{9c}$=D). The compound from Example 26 (ca. 18.9 mmol) generated above was dissolved in 2.0 M trideuteromethylamine (75 mL), stirred overnight at room temperature, and heated at 35° C. in a sealed flask for 4 hours. The precipitate was filtered and washed with small amount of methanol to give the title compound (3.11 g) as a white solid.

Example 31

(6R,12aR)-6-(2,2-dideuterobenzo[d]-1,3-dioxol-5-yl)-2-methyl-$^{13}$C-1,2,3,4,6,7,12,12a-octahydropyrazino[1',2':1,6]pyrido[3,4-b]indole-1,4-dione. A heavy-walled pressure vial is charged with a 0.96 mmol portion of product of Example 26 in 8 mL of methanol. The solution is treated with 1.9 mmol of methyl-$^{13}$C-amine hydrochloride (Isotec) and 1.9 mmol of diisopropylethylamine. The vial is sealed and heated at 50° C.

for 17 h, then the reaction is concentrated in vacuo, the residue partitioned between methylene chloride and water, and the organic layer washed with half saturated brine, dried over MgSO$_4$, and concentrated in vacuo. Crystallization from 2-propanol yields the title compound.

Example 32

6R,12aR)-6-(2,2-dideuterobenzo[d]-1,3-dioxol-5-yl)-2-methyl-$^{13}$C-1,2,3,4,6,7,12,12a-octahydropyrazino[1',2':1,6]pyrido[3,4-b]indole-1,4-dione-3-$^{13}$C. A 0.6 mmol portion of the product of example 10 is reacted with methyl-$^{13}$C-amine hydrochloride using the general procedure described in Example 31 to yield the title product.

Example 33

Inhibition of PDE5 and subtype selectivity. Activity of test compounds in PDE5 human isoform inhibition is conducted by MDS Pharma Services using essentially the protocol of Hidaka H and Asano T, Biochim. Biophys. Acta 1976 429: 485. Counterscreens using PDE1 and PDE6 are also carried out by MDS Pharma Services. These tests demonstrate nanomolar activity of each tested compound of formula II.

Example 34

2,2-dideuterobenzo[1,3]dioxole-5-carboxylic acid ethyl ester (Formula XVI). To a solution of ethyl 3,4-dihydroxybenzoate (25.3 g, 139.0 mmol) in anhydrous DMF (560 mL) was added cesium carbonate (54.3 g, 166.8 mmol) followed by dideuterodiiodomethane (45 g, 166.8 mmol). The resulting mixture was heated at 110° C. for 2 hours, cooled to room temperature, diluted with water (1.0 L), and extracted with MTBE (3×1.0 L). The combined organic layers were washed with 10 wt % potassium carbonate (1.0 L), brine (2×1.0 L), dried over sodium sulfate, and evaporated in vacuo to give the title compound as tan oil in quantitative yield.

Example 35

1-(2,2-dideuterobenzo[1,3]dioxol-5-yl)-1,1-dideuteromethanol (Formula XVII). To a solution of Example 34 (ca. 156.0 mmol) in anhydrous THF (300 mL) at −78° C. was added lithium aluminum deuteride (6.54 g, 156.0 mmol) in portions. The reaction mixture was allowed to warm to room temperature automatically, stirred at ambient temperature overnight, cooled to 0° C., quenched with saturated ammonium chloride (500 mL), and extracted with ethyl acetate (3×400 mL). The combined organic layers were dried over sodium sulfate and evaporated in vacuo to give the title compound (20.8 g, 85%) as tan oil in quantitative yield.

Example 36

2,2-dideuterobenzo[d][1,3]dioxole-5-deuterocarboxaldehyde (Formula XII wherein $X^1$=$X^2$=D and $Y^7$=D). To a solution of oxalyl chloride (13.9 mL, 160.0 mmol) in anhydrous dichloromethane (250 mL) at −78° C. was added dropwise DMSO (12.5 g, 160 mmol) dissolved in anhydrous DCM (100 mL). The mixture was stirred 1 hour at −78° C. and then a solution of Example 35 (20.8 g, 133.2 mmol) in anhydrous DCM (200 mL) was added. The newly formed reaction mixture was stirred another hour at −78° C. and triethylamine (61.7 mL, 440 mmol) was added dropwise. The reaction mixture was allowed to warm to room temperature automatically overnight. Then the reaction was quenched with water (500 mL) and the layers were split. The aqueous layer was extracted with DCM (2×400 mL). The combined organic layer was washed with brine (2×500 mL) and water (500 mL), dried over sodium sulfate, and evaporated in vacuo to give the title compound as tan oil in quantitative yield.

Example 37

(6R,12aR)-6-deutero-6-(2,2-dideuterobenzo[d]-1,3-dioxol-5-yl)-1,2,3,4,6,7,12,12a-octahydropyrazino[1',2':1,6]pyrido[3,4-b]indole-2-trideuteromethyl-1,4-dione (Formula II wherein $X^1$=$X^2$=D and $Y^7$=$Y^{9a}$=$Y^{9b}$=$Y^{9d}$=D). O-tryptophan methyl ester hydrochloride was reacted with the product from Example 36 according to the synthetic steps described for Examples 25, 26 and 30 to provide the title compound.

Example 38

(6R,12aR)-6-deutero-6-(2,2-dideuterobenzo[d]-1,3-dioxol-5-yl)-2-methyl-1,2,3,4,6,7,12,12a-octahydropyrazino[1',2':1,6]pyrido[3,4-b]indole-1,4-dione (Formula II wherein $X^1$=$X^2$=D and $Y^7$=D). O-tryptophan methyl ester hydrochloride was reacted with the product from Example 36 according to the synthetic steps described for Examples 25, 26 and 27 to provide the title compound.

Example 39

Hypotensive effects in the spontaneous hypertensive rat model. Effects of the products of examples 7, 9, 12, 18, 27 and 30 are tested by oral administration to spontaneously hypertensive rats at Cerep, using essentially the procedure of Bazil M K et. al., J. Cardiovasc. Pharmacol. 1993 22: 897 and a sample size of 8 rats per group. Each compound demonstrates significant reductions in blood pressure sustained over 8 h when dosed at 10 mg/kg.

Human Microsomal Assay: The metabolic stability of the present compounds may be evaluated in one or more microsomal assays that are known in the art. See, for example, Obach, R. S. Drug Metab Disp 1999, 27, p. 1350 "Prediction of human clearance of twenty-nine drugs from hepatic microsomal intrinsic clearance data: An examination of in vitro half-life approach and nonspecific binding to microsomes"; Houston, J. B. et al., Drug Metab Rev 1997, 29, p. 891 "Prediction of hepatic clearance from microsomes, hepatocytes, and liver slices"; Houston, J. B. Biochem Pharmacol 1994, 47, p. 1469 "Utility of in vitro drug metabolism data in predicting in vivo metabolic clearance"; Iwatsubo, T et al., Pharmacol Ther 1997, 73, p. 147 "Prediction of in vivo drug metabolism in the human liver from in vitro metabolism data"; and Lave, T. et al., Pharm Res 1997, 14, p. 152 "The use of human hepatocytes to select compounds based on their expected hepatic extraction ratios in humans"; each of which are incorporated herein in their entirety.

The objectives of this study were to determine the metabolic stability of the test compounds in pooled liver microsomal incubations and to perform full scan LC-MS analysis for the detection of major metabolites. Samples of the test compounds, exposed to pooled human liver microsomes, were analyzed using HPLC-MS (or MS/MS) detection. For determining metabolic stability, multiple reaction monitoring (MRM) was used to measure the disappearance of the test compounds. For metabolite detection, Q1 full scans were used as survey scans to detect the major metabolites.

Experimental Procedures: Human liver microsomes were obtained from Absorption Systems L.P. (Exton, Pa.). Details about the matrices used in the experiments are shown in the table below. The incubation mixture was prepared as follows:

| Reaction Mixture Composition | |
|---|---|
| Liver Microsomes | 1.0 mg/mL |
| NADPH | 1 mM |
| Potassium Phosphate, pH 7.4 | 100 mM |
| Magnesium Chloride | 10 mM |
| Test Compound | 1 μM |

Incubation of Test Compounds with Liver Microsomes: The reaction mixture, minus cofactors, was prepared. An aliquot of the reaction mixture (without cofactors) was incubated in a shaking water bath at 37° C. for 3 minutes. Another aliquot of the reaction mixture was prepared as the negative control. The test compound was added into both the reaction mixture and the negative control at a final concentration of 1 μM. An aliquot of the reaction mixture was prepared as a blank control, by the addition of plain organic solvent (not the test compound). The reaction was initiated by the addition of cofactors (not into the negative controls), and then incubated in a shaking water bath at 37° C. Aliquots (200 μL) were withdrawn in triplicate at 0, 15, 30, 60, and 120 minutes and combined with 800 μL of ice-cold 50/50 acetonitrile/dH$_2$O to terminate the reaction. The positive controls, testosterone and propranolol, were run simultaneously with the test compounds in separate reactions.

All samples were analyzed using LC-MS (or MS/MS). An LC-MRM-MS/MS method was used for metabolic stability. Also, Q1 full scan LC-MS methods were performed on the blank matrix and the test compound incubation samples. The Q1 scans served as survey scans to identify any sample unique peaks that might represent the possible metabolites. The masses of these potential metabolites can be determined from the Q1 scans.

Results: Metabolic Stability:

| Example | R$_1$ | R |
|---|---|---|
| Control-tadalafil | | |
| A | CH3 | H |
| B | CH3 | D |
| C | CD3 | H |
| D | CD3 | D |

Test compounds A-D were evaluated in the human microsomal assay described above along with tadalafil as a control. After 60 minutes of exposure in the microsomal assay, deuterated analogs A-D were more resistant to microsomal degradation than non-deuterated tadalafil. The results indicated that the deuterium substitution in the compounds of the invention was effective in slowing cytochrome-mediated oxidation.

All references cited herein, whether in print, electronic, computer readable storage media or other form, are expressly incorporated by reference in their entirety, including but not limited to, abstracts, articles, journals, publications, texts, treatises, technical data sheets, internet web sites, databases, patents, patent applications, and patent publications.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

I claim:

1. An isolated compound of Formula II:

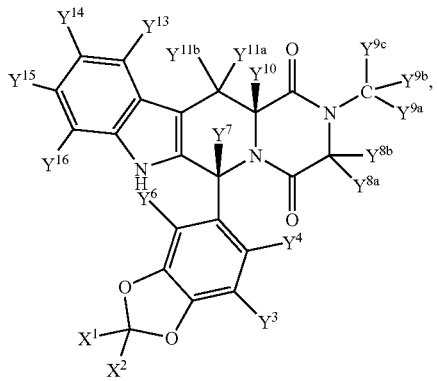

(II)

or a pharmaceutically acceptable salt thereof; wherein:

$X^1$ and $X^2$ are simultaneously fluoro;

each of $Y^3$, $Y^4$, $Y^6$, $Y^7$, $Y^{8a}$, $Y^{8b}$, $Y^{9a}$, $Y^{9b}$, $Y^{9c}$, $Y^{10}$, $Y^{11a}$, $Y^{11b}$, $Y^{13}$, $Y^{14}$, $Y^{15}$, and $Y^{16}$ is independently selected from deuterium or hydrogen;

the hydrogen attached to the indole nitrogen is optionally replaced by deuterium; and each carbon is independently optionally replaced by $^{13}$C.

2. The compound or salt according to claim 1, having a formula:

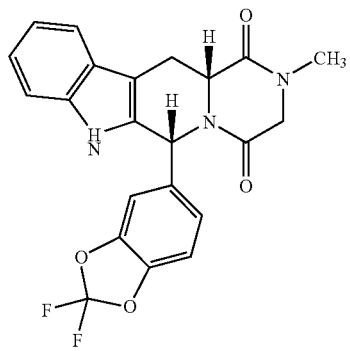

wherein the hydrogen attached to the indole nitrogen is not replaced by deuterium and wherein no carbon atoms are replaced by $^{13}C$.

3. The compound or salt according to claim 1, wherein all hydrogen atoms not replaced by deuterium and all carbon atoms not replaced by $^{13}C$ are present at their natural isotopic abundance.

4. A pharmaceutical composition comprising an effective amount of a compound or salt according to claim 1; and a pharmaceutically acceptable carrier.

* * * * *